United States Patent
Cespedes et al.

(10) Patent No.: US 10,478,101 B1
(45) Date of Patent: Nov. 19, 2019

(54) CONTINUOUS GLUCOSE MONITORING BASED ON REMOTE SENSING OF VARIATIONS OF PARAMETERS OF A SIC IMPLANTED ANTENNA

(71) Applicants: Fabiola Araujo Cespedes, Temple Terrace, FL (US); Stephen E. Saddow, Tampa, FL (US); Christopher Leroy Frewin, Richardson, TX (US); Erdem Topsakal, Starkville, MS (US)

(72) Inventors: Fabiola Araujo Cespedes, Temple Terrace, FL (US); Stephen E. Saddow, Tampa, FL (US); Christopher Leroy Frewin, Richardson, TX (US); Erdem Topsakal, Starkville, MS (US)

(73) Assignee: University of South Florida, Tampa, FL (US)

( * ) Notice: Subject to any disclaimer, the term of this patent is extended or adjusted under 35 U.S.C. 154(b) by 447 days.

(21) Appl. No.: 15/286,173

(22) Filed: Oct. 5, 2016

Related U.S. Application Data

(60) Provisional application No. 62/237,280, filed on Oct. 5, 2015.

(51) Int. Cl.
*A61B 5/00* (2006.01)
*A61B 5/145* (2006.01)

(52) U.S. Cl.
CPC ........ *A61B 5/14532* (2013.01); *A61B 5/0002* (2013.01)

(58) Field of Classification Search
CPC .............................. A61B 5/14532; A61B 5/00
See application file for complete search history.

(56) References Cited

U.S. PATENT DOCUMENTS

| 6,441,354 B1 * | 8/2002 | Seghatol ................. | A61C 5/00 |
| | | | 219/679 |
| 2015/0051466 A1 * | 2/2015 | Afroz ..................... | A61B 5/686 |
| | | | 600/377 |

(Continued)

FOREIGN PATENT DOCUMENTS

WO      2013138275 A1     9/2013

OTHER PUBLICATIONS

Soontornpipit, "Design of an Implantable Antenna Feasibility Study for Continuous Glucose Monitoring," ECTI Transactions on Electrical Eng., Electronics, and Communications vol. 12, No. 1 Feb. 2014 (Year: 2014).*

(Continued)

*Primary Examiner* — Eric J Messersmith
(74) *Attorney, Agent, or Firm* — Paul Murty; Nilay J. Choksi; Smith & Hopen, P.A.

(57) ABSTRACT

A passive sensing continuous glucose monitoring system and method of use thereof. The system includes a passive antenna formed of biocompatible silicon carbide (SiC), modeled to a desired frequency, which is permanently implanted subcutaneously. The system further includes an external-to-the-body transmitting antenna to detect changes in the blood glucose level by sending a radio signal at the frequency of the implanted passive antenna into the body. This signal is received and reflected by the passive antenna, and the reflected signal is then received at an external-to-the-body receiving antenna. Changes in the glucose level lead to modifications in the signal and can be used to determine the blood glucose level externally.

15 Claims, 28 Drawing Sheets

(56) References Cited

U.S. PATENT DOCUMENTS

2016/0338625 A1* 11/2016 Min ..................... A61B 5/1473
2017/0181658 A1* 6/2017 Dettmann ............ A61B 5/0031

OTHER PUBLICATIONS

User's Guide, Agilent Technologies 8719D/20D/22D Network Analyzers (Year: 2012).*

Fast Facts: Data and Statistics about Diabetes, American Diabetes Association, Sep. 2015.

Executive Summary: Standards of Medical Care in Diabetes—2013, Diabetes Care, vol. 36, pp. S4-S10, Jan. 1, 2013.

W. Myers, Managing Diabetes With Continuous Glucose Monitoring, http://www.everydayhealth.com/diabetes/managing-diabetes-with-continuous-glucose-monitoring.aspx, Last Updated Feb. 12, 2013. Accessed Oct. 2, 2015.

L. Czupryniak, et al., Self-Monitoring of Blood Glucose in Diabetes: From Evidence to Clinical Reality in Central and Eastern Europe—Recommendations from the International Central-Eastern European Expert Group, Diabetes Technology & Therapeutics, vol. 16, No. 7, pp. 460-475, 2014.

J. L. Smith, The Pursuit of Noninvasive Glucose: "Hunting the Deceitful Turkey", 4 ed., 2015.

C.-F. So, et al., Recent advances in noninvasive glucose monitoring, Medical Devices: Evidence and Research, (Auckland, N.Z.), vol. 5, pp. 45-52, 2012.

N. S. Oliver, et al., Glucose sensors: a review of current and emerging technology, Diabetic Medicine, vol. 26, pp. 197-210, Apr. 2009.

Y. Onuki, et al., A Review of the Biocompatibility of Implantable Devices: Current Challenges to Overcome Foreign Body Response, Journal of Diabetes Science and Technology (Online), vol. 2, issue 6, pp. 1003-1015, Nov. 2008.

H. E. Koschwanez, et al., In Vitro, In Vivo and Post Explantation Testing of Glucose-Detecting Biosensors: Current Methods and Recommendations, Biomaterials, vol. 28, No. 25, pp. 3687-3703, 2007.

S. Afroz, A Biocompatible SiC RF Antenna for In-vivo Sensing Applications, Ph.D., Electrical Engineering, University of South Florida, 2013.

S. Afroz, et al., Implantable SiC based RF antenna biosensor for continuous glucose monitoring, in IEEE Sensors, Baltimore, Maryland USA, 2013.

C. L. Frewin, et al., Single-Crystal Cubic Silicon Carbide: An in vivo biocompatible semiconductor for brain machine interface devices, Engineering in Medicine and Biology Society,EMBC, 2011 Annual International Conference of the IEEE, Boston, MA, 2011, pp. 2957-2960.

C. L. Frewin, et al., Silicon Carbide Neural Implants: in vivo Neural Tissue Reaction, Neural Engineering (NER), 6th International IEEE/EMBS Conference on Neural Engineering, San Diego, CA, Nov. 2013, pp. 661-664.

K.D. Nguyen, et al., A wearable sensing system for tracking and monitoring of functional arm movement, IEEE/ASME Trans. Mechatronics, vol. 16, No. 2, pp. 213-220, Apr. 2011.

A. U. Alahakone, et al., A real-time system with assistive feedback for postural control in rehabilitation, IEEE/ASME Trans. Mechatronics, vol. 15, No. 2, pp. 226-233, Apr. 2010.

T. Karacolak, et al., Design of a Dual-Band Implantable Antenna and Development of Skin Mimicking Gels for Continuous Glucose Monitoring, IEEE Transactions on Microwave Theory and Techniques, vol. 56, No. 4, pp. 1001-1008, Apr. 2008.

A. K. Skrivervik, et al., Design Strategies for Implantable Antennas, Laboratoire d'Electromagnetisme et d'Acoustique, Ecole Polytechnique Federale de Lausanne, Station 11, CH-1015 Lausanne Switzerland, 2011.

M. Hoskins, GlySens (Still) Developing Implantable CGM, Diabetes Mine, Healthline.com, May 2014, Accessed Jan. 4, 2017.

L. L. Hench, et al. Biocompatibility of silicates for medical use, Ciba Foundation Symposium—1986 Silicon Biochemistry, vol. 121, pp. 231-246.

C. Coletti, et al., Biocompatibility and wettability of crystalline SiC and Si surfaces, Proceedings of the 29th International conference of the IEEE EMBS, Lyon, France, Aug. 23-26, 2007, pp. 5849-5852.

T. V. Kumari, et al., Cell surface interaction in the study of biocompatibility, Trends Biomaterials and Artificial Organs, Society for Biomaterials and Artificial Organs Audience, vol. 15, issue 2, pp. 37-41, 2002.

R. D. Beach, et al., Towards a miniature implantable in vivo telemetry monitoring system dynamically configurable as a potentiostat or galvanostat for two- and three-electrode biosensors, IEEE Trans. Instrument. Meas., vol. 54, No. 1, Feb. 2005.

S. Kim, et al., Noninvasive in vitro measurement of pig-blood D-glucose by using a microwave cavity sensor, Diabetes Research and Clinical Practice vol. 96, pp. 379-384, 2012.

E. Topsakal, et al., Glucose-Dependent Dielectric Properties of Blood Plasma, URSI, IEEE, 2011.

H.P. Schwan, Electrode polarization impedance and measurements in biological materials, Annals New York Academy of Sciences, pp. 191-209, 1968.

S. C. Hagness, et al., Wideband Ultra-Low Reverberation Antenna for Biological Sensing, Electronics Letters, vol. 33, No. 19, pp. 1594-1595, Sep. 11, 1997.

Y. Hayashi, et al., Dielectric spectroscopy study of specific glucose influence on human erythrocyte membranes, Journal of Physics D: Applied Physics, vol. 36, pp. 369-374, 2003.

LF-2.7 GHz RF/IF Gain and Phase Detector, AD8302, Analog Devices, www.analog.com, Analog Devices, Inc. 2002.

P. Holt, Blood glucose monitoring in diabetes, Nursing Standard, vol. 28, pp. 52-58, 2014.

* cited by examiner

| Name | Value | Unit | Evaluated Value |
|---|---|---|---|
| subX | 3.5 | cm | 3.5cm |
| subY | 4.4 | cm | 4.4cm |
| subH | 50 | mil | 50mil |
| patchX | 2.64 | cm | 2.64cm |
| patchY | 1.95 | cm | 1.95cm |
| FeedWidth | 0.119 | cm | 0.119cm |
| InsetGap | 0.06 | cm | 0.06cm |
| InsetDistance | 0.704 | cm | 0.704cm |
| FeedLength | 1.992 | cm | 1.992cm |
| yy | 0.1 | cm | 0.1cm |
| yyy | subY/2-patchY/2+yy+insetdistance-feedlength | | 0.037cm |

*FIG. 9B*

| | |
|---|---|
| frequency n | address n |
| ⋮ | ⋮ |
| frequency 6 | address 6 |
| frequency 5 | address 5 |
| frequency 4 | address 4 |
| frequency 3 | address 3 |
| frequency 2 | address 2 |
| frequency 1 | address 1 |
| No. frequency | address 0 |

*FIG. 17*

| | |
|---|---|
| G_signal data n [ | address m+q |
| ⋮ | ⋮ |
| G_signal data 6 [freq | address 6+q |
| G_signal data 5 [freq | address 5+q |
| G_signal data 4 [freq | address 4+q |
| G_signal data 3 [freq | address 3+q |
| G_signal data 2 [freq | address 2+q |
| G_signal data 1 [freq | address 1+q |
| m | address 0+q |

*FIG. 18*

CONTINUOUS GLUCOSE MONITORING BASED ON REMOTE SENSING OF VARIATIONS OF PARAMETERS OF A SIC IMPLANTED ANTENNA

CROSS-REFERENCE TO RELATED APPLICATIONS

This nonprovisional application is claims priority to U.S. Provisional Patent Application No. 62/237,280, entitled "Continuous Glucose Monitoring Based on Remote Sensing of Variations of Parameters of a SiC Implanted Antenna", filed Oct. 5, 2015 by the same inventors, the entirety of which is incorporated herein by reference.

OTHER RELATED APPLICATIONS

This nonprovisional application relates to U.S. patent application Ser. No. 14/383,967, entitled "Implantable Biocompatible SiC Sensors", the entirety of which is incorporated herein by reference.

BACKGROUND OF THE INVENTION

1. Field of the Invention

This invention relates, generally, to glucose monitoring. More specifically, it relates to passive sensing continuous glucose monitoring systems.

2. Brief Description of the Prior Art

Glucose Monitoring

The American Diabetes Association estimates that nearly 10% of the U.S. population has diabetes and that, by 2050, 1 in 3 Americans will have diabetes. Diabetes mellitus is a metabolic disease in which the body is unable to produce or properly use insulin, leading to elevated glucose levels in the blood, known as hyperglycemia. A person with frequent or extended episodes of hyperglycemia can suffer from complications in the nervous system, blood vessels and other organs, as well as heart disease, kidney disease, strokes, vision loss, and amputation ["Fast Facts: Data and Statistics about Diabetes," A. D. Association, Ed., ed: American Diabetes Association, 2015; "Executive Summary: Standards of Medical Care in Diabetes—2013," Diabetes Care, vol. 36, pp. S4-S10, Jan. 1, 2013 2013; P. Holt, "Blood glucose monitoring in diabetes," Nursing Standard, vol. 28, pp. 52-58, 2014 Mar. 11 2014]. Therefore, maintaining a healthy glucose level is essential in a person's life.

Clinical studies have proven that self-monitoring of glucose levels helps treatment decisions in insulin and non-insulin use patients with diabetes ["Executive Summary: Standards of Medical Care in Diabetes—2013," Diabetes Care, vol. 36, pp. S4-S10, Jan. 1, 2013 2013]. Self-monitoring also reduces the frequency of hypoglycemia thus greatly extending patient quality of life. Although there are many instantaneous blood glucose monitors on the market (e.g., finger pricking blood sampling), these provide only a single instantaneous level at that time, and multiple daily use leads to patient discomfort. Continuous monitoring of the blood sugar levels is much more useful, especially for individuals who are at high risk [W. Myers. (2013). Managing Diabetes with Continuous Glucose Monitoring].

All continuous glucose monitoring (CGM) systems that are currently approved by the U.S. Food and Drug Administration (FDA) require the insertion of a disposable needle-like device into the body, which lasts only up to a week [P. Holt, "Blood glucose monitoring in diabetes," Nursing Standard, vol. 28, pp. 52-58, 2014 Mar. 11 2014; W. Myers. (2013). Managing Diabetes with Continuous Glucose Monitoring; L. Czupryniak, L. Barkai, S. Bolgarska, A. Bronisz, J. Broz, K. Cypryk, et al., "Self-Monitoring of Blood Glucose in Diabetes: From Evidence to Clinical Reality in Central and Eastern Europe—Recommendations from the International Central-Eastern European Expert Group," Diabetes Technology & Therapeutics, vol. 16, pp. 460-475, 2014]. Unfortunately, a long-term in vivo glucose sensor has yet to enter the market with typical maximum time of use on the order of 4-7 days.

In addition, these CGM systems also require calibration four (4) times a day with the finger-sticking blood sample technique, since the measurement is not done directly on the blood glucose, but rather measures the glucose of the interstitial fluid (ISF) [P. Holt, "Blood glucose monitoring in diabetes," Nursing Standard, vol. 28, pp. 52-58, 2014 Mar. 11 2014; L. Czupryniak, L. Barkai, S. Bolgarska, A. Bronisz, J. Broz, K. Cypryk, et al., "Self-Monitoring of Blood Glucose in Diabetes: From Evidence to Clinical Reality in Central and Eastern Europe—Recommendations from the International Central-Eastern European Expert Group," Diabetes Technology & Therapeutics, vol. 16, pp. 460-475, 2014]. These CGM systems, such as those marketed by Medronic, DexCom STS and Abbott FreeStyle Navigator, can result in elevated costs, not only due to the device itself, but the cost of the disposable sensor needles, adding a monthly cost of around $300 [W. Myers. (2013). Managing Diabetes With Continuous Glucose Monitoring]. Of course, the patient would prefer a less invasive method to monitor the glucose levels, and many have been tried, but have experienced various issues. Further, conventional finger-pricking and CGM systems can result in painful glucose samples for the patient, are costly long-term and not reliable due to variation in blood sampling by the patient, especially for those with severely degraded health and mobility.

Most non-invasive glucose monitoring systems face the challenge of being susceptible to external interference from other factors such as body temperature, perspiration, skin moisture, changes in skin thickness and body movement [J. L. Smith, The Pursuit of Noninvasive Glucose: "Hunting the Deceitful Turkey", 4 ed., 2015; C.-F. So, K.-S. Choi, T. K. S. Wong, and J. W. Y. Chung, "Recent advances in noninvasive glucose monitoring," Medical Devices (Auckland, N.Z.), vol. 5, pp. 45-52, Jun. 29, 2012; N. S. Oliver, C. Toumazou, A. E. G. Cass, and D. G. Johnston, "Glucose sensors: a review of current and emerging technology," Diabetic Medicine, vol. 26, pp. 197-210, 2009]. For instance, infrared spectroscopy, including near infrared (NIR) spectroscopy and far infrared (FIR) spectroscopy, depend on optical transmission and reflection measurements, which are subject to interference from external factors that affect the reflection measurement. For this reason, NIR requires frequent recalibration.

In FIR, the emitted energy that is absorbed by glucose and measured is so small that this method has not yet been proven to be accurate. In other methods, such as Raman spectroscopy, the measurement of light scattering that is caused by generated oscillations such as laser oscillation in the ocular fluid is subject to interference from other molecules. In thermal spectroscopy, the infrared (IR) radiation that is emitted from the body is also affected by other factors external to glucose concentration. Another example is the technology based on measuring the ISF that is secreted from the skin to measure the glucose levels, which presents a time lag deficiency. Overall, non-invasive technologies lack accuracy due to being susceptible to external factors such as transpiration, temperature, positioning, and/or displaying time lag problems of up to 20 minutes, making the technology unreliable.

Another approach to self-monitoring glucose is a fully implantable glucose monitoring system. These medical devices face other types of challenges, such as in vivo inflammatory reaction and foreign body reaction, posing risk for the patients and hence the need for biocompatibility tests on any implantable device [N. S. Oliver, C. Toumazou, A. E. G. Cass, and D. G. Johnston, "Glucose sensors: a review of current and emerging technology," Diabetic Medicine, vol. 26, pp. 197-210, 2009]. Other considerations include operating under the communication regulations and standard, in frequencies allocated for this purpose, design approach to achieve miniaturization, and parameters of the antenna (e.g., bandwidth, specific absorption rate, impedance matching and others). In particular, the use of RFIDs and systems to perform biotelemetry have been reported and it is now possible to implant wireless sensors inside the human body to monitor various bodily functions and transmit health related information outside of the human body for remote monitoring [K. D. Nguyen, I. M. Chen, Z. Q. Luo, S. H. Yeo, and H. B. L. Duh, "A wearable sensing system for tracking and monitoring of functional arm movement," *IEEE/ASME Trans. Mechatronics*, vol. 16, no. 2, pp. 213-220, April 2011; A. U. Alahakone and S. Senanayake, "A real-time system with assistive feedback for postural control in rehabilitation," *IEEE/ASME Trans. Mechatronics*, vol. 15, no. 2, pp. 226-233, April 2010; Tutku Karacolak, Aron Z. Hood, Erdem Topsakal, "Design of a Dual-Band Implantable Antenna and Development of Skin Mimicking Gels for Continuous Glucose Monitoring," *IEEE Transactions on Microwave Theory and Techniques*, Vol. 56, No. 4, April 2008].

However, many implants have difficulties reliably functioning in vivo due to the inflammatory response to foreign materials; the endpoint of this response is a close-knit encapsulation around the object, that is generally 100 microns thick, which not only acts as a diffusion barrier to enzymatic activity (as is used in current FDA-approved CGM methods) but is also electrically insulating. Therefore, long-term implantations are subject to gradual loss of sensor functionality and stability due to fibrosis encapsulation and tissue changes in proximity of the sensor [Y. Onuki, U. Bhardwaj, F. Papadimitrakopoulos, and D. J. Burgess, "A Review of the Biocompatibility of Implantable Devices: Current Challenges to Overcome Foreign Body Response," Journal of diabetes science and technology (Online), vol. 2, pp. 1003-1015, November 2008; H. E. Koschwanez and W. M. Reichert, "In Vitro, In vivo and Post Explantation Testing of Glucose-Detecting Biosensors: Current Methods and Recommendations," Biomaterials, vol. 28, pp. 3687-3703, Apr. 19, 2007]. In response, some implantable devices, including antennas, are coated with biocompatible materials, but in the aspect of communicating externally from the body, this adds to the effects of sensor encapsulation [SKRIVERVIK, A., MERLI, F., Design Strategies for Implantable Antennas. Laboratoire d'Electromagnetisme et d'Acoustique, Ecole Polytechnique Federale de Lausanne, Station 11, CH-1015 Lausanne Switzerland (2011)].

However, in addition to the issue of biocompatibility, the life cycle of the implanted device is relevant to factors such as the sensing mechanism inside the body and the energy required to function properly. Current long-term implantable glucose sensing approaches are predicted to last only a maximum of 18 months in vivo after implantation [GlySens (Still) Developing Implantable CGM. Diabetes Mine. May 2014]. As can be seen, several approaches to develop a CGM have been proposed, but none have been fully developed towards a complete sensor platform.

Silicon/Silicon Carbide

Silicon carbide (SiC) is a well-known wide-band gap semiconductor traditionally used in power electronics and solid-state lighting due to its extremely low intrinsic carrier concentration and high thermal conductivity. What is only recently being discovered is that it possesses excellent compatibility within the biological world. One way to produce a "smart" device is to fabricate it using electrical components that allow for the control of current flow. Semiconductor materials are the backbone of these types of electronic devices, with silicon (Si) being the mainstay material of choice due to a myriad of fabrication techniques. However, Si has proven to have low levels of bio- and hemocompatibility, and therefore long-term implantable technology based on this material has displayed variable performance reliability [L. L. Hench and J. Wilson, "Biocompatibility of silicates for medical use," in Ciba Foundation Symposium—Silicon Biochemistry. vol. 121, D. Evered and M. O'Connor, Eds., ed Chichester, UK: John Wiley & Sons, 1986, pp. 231-253]. The current inventors have previously demonstrated that the only purely cubic form, 3C—SiC, is effective for many biomedical applications and is also hemocompatible (see [S. E. Saddow and A. Agrawal, Editors *Advances in Silicon Carbide Processing and Applications,* 2004 Artech House ISBN 1-58053-740-5]). When antenna sensors are fabricated using a fully biocompatible and hemocompatible material, such as 3C—SiC, these antenna sensors can curtail adverse tissue reaction, which can endanger the life of a patient [Coletti C, Jaroszeski, M J, Pallaoro A, Hoff A M, Iannotta S, Saddow, S E., "Biocompatibility and wettability of crystalline SiC and Si surfaces." Proceedings of the 29th International conference of the IEEE EMS; Lyon, France. p. 5849-52, Aug. 23-26, 2007; Kumari T V, Vasudev U, Kumar A, Menon B. 'Cell surface interaction in the study of biocompatibility.' *Trends Biomat Artif Organs,* 15, 2002: 37-41].

Many of today's point-of-use healthcare systems are hybrid implantable systems that combine radio frequency (e.g., Wi-Fi) and biosensor technologies. The biosensors usually rely on relevant physiological parameters for continuous monitoring and an integrated antenna is employed in order to send the received data to an external receiver [R. D. Beach, R. W. Conlan, M. C. Godwin, and F. Moussy, "Towards a miniature implantable in vivo telemetry monitoring system dynamically configurable as a potentiostat or galvanostat for two- and three-electrode biosensors," *IEEE Trans. Instrument. Meas.*, vol. 54, no. 1, February 2005]. Therefore, implantable antennas have attracted considerable attention in recent years as a potential solution for communicating with these implantable biosensors.

In the case of electromagnetic coupling based sensors, a SiC antenna sensor does not require a direct interface with the interstitial fluid, thus offering a simpler monitoring technique as compared to conventional sensors. The antenna responds by exhibiting a shift in its resonance frequency as the varying glucose concentration changes the effective complex permittivity of the blood [S. Kim, H. Melikyan, J. Kim, A. Babajanyan, J-Ha Lee, L. Enkhtur, B. Friedman, K. Lee, "Noninvasive in vitro measurement of pig-blood D-glucose by using a microwave cavity sensor" *Diabetes Research and Clinical Practice* 96, 379-384, 2012].

The current inventors previously disclosed a method that would allow the monitoring of glucose via implantable device via a CGM sensor employing RF signals [U.S. Patent Application Publication No. 2015/0051466 A1; S. Afroz, "A Biocompatible SiC RF Antenna for In-vivo Sensing Applications," Ph.D., Electrical Engineering, University of South Florida, 2013; S. Afroz, S. W. Thomas, G. Mumcu, and S. E. Saddow, "Implantable SiC based RF antenna biosensor for continuous glucose monitoring," in IEEE Sensors, Baltimore, Md. USA, 2013]. In short, the device used an implanted device to transmit a signal through a specialized antenna to an external receiver. The shift in the received transmission could be correlated to the glucose level at the time of the transmission. This device/methodology used SiC as the main material for the production of the device, both the antenna and hermetic coatings, due to its overall electrical properties coupled with excellent biocompatibility, thus removing the need to encase this biomedical device with biocompatible materials and addresses the short lifetime issue of current sensors. This was demonstrated in two separate animal models, namely pigs and mice; SiC did not produce appreciable chronic inflammatory reactions after one (1) month of implantation [S. Afroz, "A Biocompatible SiC RF Antenna for In-vivo Sensing Applications," Ph.D., Electrical Engineering, University of South Florida, 2013; S. Afroz, S. W. Thomas, G. Mumcu, and S. E. Saddow, "Implantable SiC based RF antenna biosensor for continuous glucose monitoring," in IEEE Sensors, Baltimore, Md. USA, 2013; C. L. Frewin, C. Locke, S. E. Saddow, and E. J. Weeber, "Single-Crystal Cubic Silicon Carbide: An in vivo biocompatible semiconductor for brain machine interface devices," in Engineering in Medicine and Biology Society, EMBC, 2011 Annual International Conference of the IEEE, Boston, Mass., 2011, pp. 2957-60; C. L. Frewin, C. Locke, L. Mariusso, E. J. Weeber, and S. E. Saddow, "Silicon Carbide Neural Implants: in vivo Neural Tissue Reaction," Neural Engineering (NER), 6th International IEEE/EMBS Conference on, pp. 661-664, 2013].

Unlike biosensors that require direct contact with ISFs to trigger chemical reactions to operate, this biocompatible SiC sensor did not require a direct interface to bodily fluids. The sensing mechanism was based upon a shift in the antenna resonant frequency as a function of change in glucose levels which electrically manifests itself as a change in blood permittivity and conductivity. When placed near a blood vessel, such an antenna can potentially sense the variation in blood permittivity, which is strongly dependent on glucose level [E. Topsakal, T. Karacolak, and E. C. Moreland, "Glucose-Dependent Dielectric Properties of Blood Plasma", *URSI, IEEE,* 2011]. The permittivity varies with blood glucose altering antenna parameters, such as input impedance and reflection coefficient, $S_{11}$ [Balanis, Constantine A., *Antenna Theory, Analysis and Design,* Third Edition, 2005: ISBN: 0-471-66782-X]. For diabetic patients, the concentration of other minerals present in the blood, such as calcium, chloride, potassium, and magnesium, have been shown to not vary as significantly as glucose [Schwan H P., "Electrode polarization impedance and measurements in biological materials", *Ann. N.Y. Acad. Sci.* 1968:148-191; S. C. Hagness, A. Taflove, and J. E. Bridges, "Wideband Ultra-Low Reverberation Antenna for Biological Sensing," *Electron. Lett.,* vol. 33, pp. 1594-1595, Sep. 11, 1997; Hayashi Y, Livshits L, Caduff A, Feldman Y, "Dielectric spectroscopy study of specific glucose influence on human erythrocyte membranes", *J Phys D* 2003; 36: 369-74]. Therefore, changes in permittivity are utilized to estimate the patient's plasma glucose levels.

To test the sensor as a function of glucose level, measurements using synthetic body fluid (SBF), which is electrically equivalent to blood plasma, and pig blood were performed in vitro. Changes in sensor performance to varying glucose levels were measured and a shift in resonant frequency to lower values observed with increasing glucose level. Specifically, the SiC biosensor was within a fatty tissue region that is in close proximity to a blood vessel. For demonstrating the sensing mechanism and characterizing the sensitivity, different glucose level measurements were performed in vitro by using a 2-layered fat and blood layer model as shown in FIG. 1A (the 4H—SiC microstrip patch antenna itself can be seen in FIG. 1B). Two types of blood media were used; blood mimicking liquid and pig blood. In both instances the fatty layer was synthesized with fat mimicking liquid. Using this in vitro model, a glucose level variation from 120 mg/dl to 530 mg/dl was found to provide 40 MHz and 26 MHz shifts in the maximum return loss of the sensor for blood mimicking liquid and pig blood, respectively.

One major issue with this device/methodology, however, is that the design requires implanted electronics to produce a signal that is then transmitted to an external source. It also requires the inclusion of two antennas in vivo. The electronics would also require a power source, or a means of receiving adequate transmitted power. Ultimately, this would increase the size and complexity of the implant, and creates multiple points of failure which may be difficult to address after the initial implantation. Further, there was no sensor platform designed to obtain the glucose results outside the body, as the research concentrated only on the concepts of variation of parameters in the antenna itself. No mechanism was proposed to detect variations outside of the body. Finally, the in vivo trial was of biocompatibility of the antenna itself, so no in vivo functional testing was performed.

Accordingly, what is needed is a passive sensor that can be utilized long-term within a patient or subject for continuous and accurate glucose monitoring. However, in view of the art considered as a whole at the time the present invention.

Accordingly, what is needed is a passive sensor that can be utilized long-term within a patient or subject for continuous glucose monitoring. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved continuous glucose monitoring system, and method of use thereof, is now met by a new, useful, and nonobvious invention.

In an embodiment, the current invention is a passive sensing continuous glucose monitoring system for continuously monitoring a glucose level in a patient or subject. In another embodiment, the current invention is a method of continuously and passively sensing and monitoring glucose level in a patient or subject, in other words a method of using the passive sensing continuous glucose monitoring system. The system includes an external transmitting antenna positioned outside the patient's body. The transmitting antenna transmits an RF signal into the patient's body. A passive internal antenna is positioned subdermally within the patient's body (e.g., in a fat layer of the patient near a blood vessel of the patient) and receives the RF signal from the transmitting antenna. The internal antenna then reflects the signal back out of the body. Resonant frequency experienced by the internal antenna varies as blood glucose levels in the patient change. The internal antenna may be formed of silicon carbide, further optionally with amorphous silicon carbide insulation.

An external receiving antenna is positioned outside the patient's body in proximity (e.g., adjacent) to the transmitting antenna and receives the reflected RF signal from the internal antenna. The internal antenna is mounted directly towards the transmitting and receiving antennas. The RF signal received by the receiving antenna is translated into a measure of the patient's glucose level. The system further includes one or more power sources for powering the transmitting and receiving antennas, along with a display for displaying the measure of patient's glucose level. In a preferred embodiment, the system operates in the ISM radio band.

The system may further include a controller input, such as a keyboard, to control subsystem options, including calibration, storage, history, and default value restore.

The transmitting antenna may include a microcontroller (e.g., low power microcontroller) and a signal generator (e.g., direct digital synthesis integrated circuit, a phase-locked loop with voltage control oscillator). The microcontroller controls frequency and times of the RF signal generated by the signal generator, such that the microcontroller controls the frequency sweep transmitted by the transmitting antenna.

The receiving antenna may include a microcontroller and an RF-to-DC converter that receives the reflected RF signal and converts that signal to a digital value that is transmitted to the microcontroller. In turn, the microcontroller stores the digital value in a storage module, processes the digital value into the patient's glucose level, and displays the glucose level on the display.

In an alternative embodiment, the transmitting antenna includes a signal generator and the receiving antenna includes an RF-to-DC converter. Both antennas are in communication with a microcontroller that is coupled to the display.

In a separate embodiment, the current invention is a system and method as discussed above, and including any one or more—or even all—of the foregoing features and characteristics.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 8 further depicts preliminary ISM band remote read CGM sensing system data. Insets cross section of experimental setup and 3D view, respectively. Note useful glucose detection up to ~200 mg/dl.

FIG. 9B depicts antenna dimensions of the band patch antenna of FIG. 9A.

In FIGS. 11A-11B, simulation was performed using ANSYS HFSS. Note that a symmetrical beam profile, as expected, is simulated and the resonant frequency of 2.45 GHz achieved with a return loss of ~17.5 dB in free space.

FIG. 17 shows that frequencies are stored in a section of the data memory.

FIG. 18 shows that the glucose signal for each frequency will be stored in a section of the data memory at the time of reception of the data.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

In certain embodiments, the current invention is a passive sensing continuous glucose monitoring system (PSCGM). The system includes a single implanted antenna that functions as a passive sensor, with all electronics and power sources located external to the patient's body. The passive antenna can be formed using the same materials as disclosed in the related patent application (U.S. patent application Ser. No. 14/383,967) and placed sub-dermally in the fat layer. The parameters of this implanted antenna, particularly the resonant frequency, vary as a function of the changes in blood glucose levels.

Figure 1A:
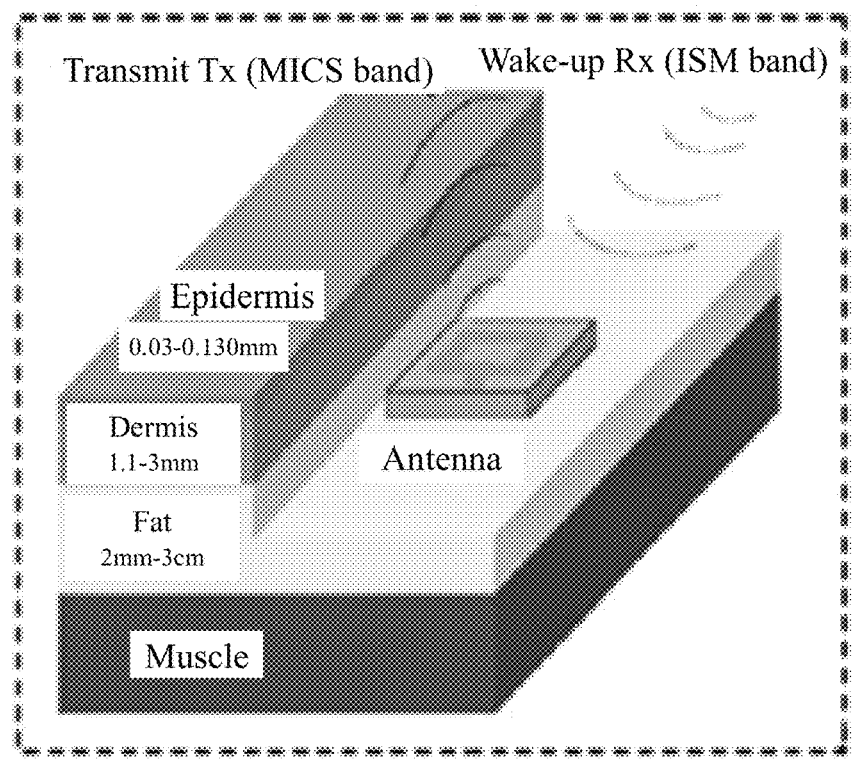
FIG. 1A is a schematic of sensor placement within the body, according to a previous work by the current inventors.
Figure 1B:
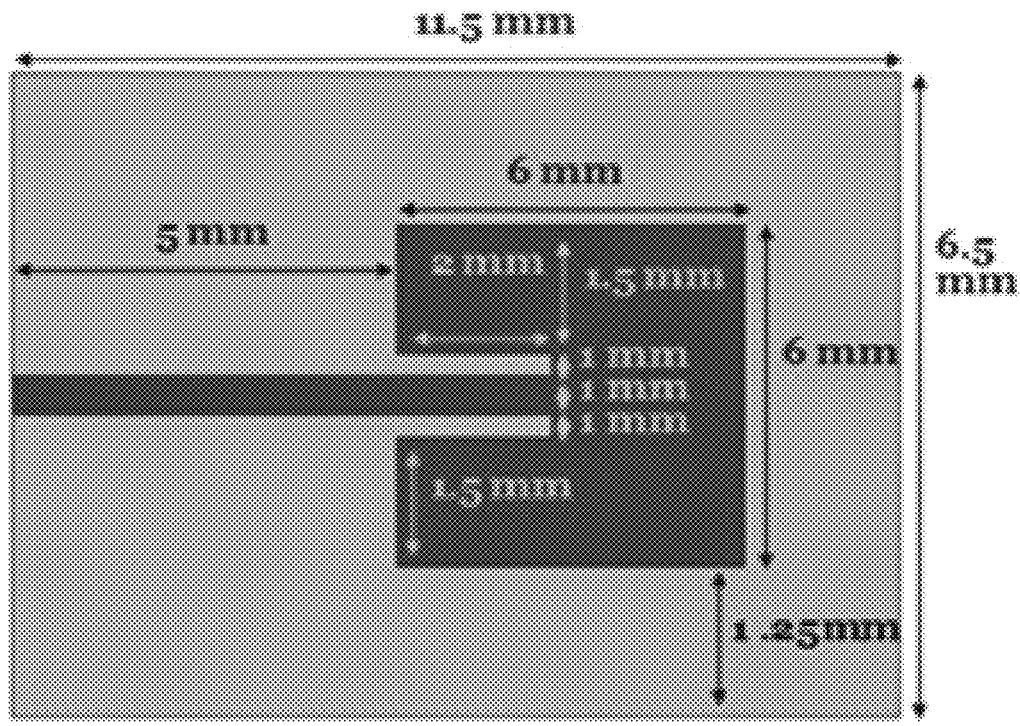
FIG. 1B depicts 4H—SiC microstrip patch antenna dimensions.
Figure 2:
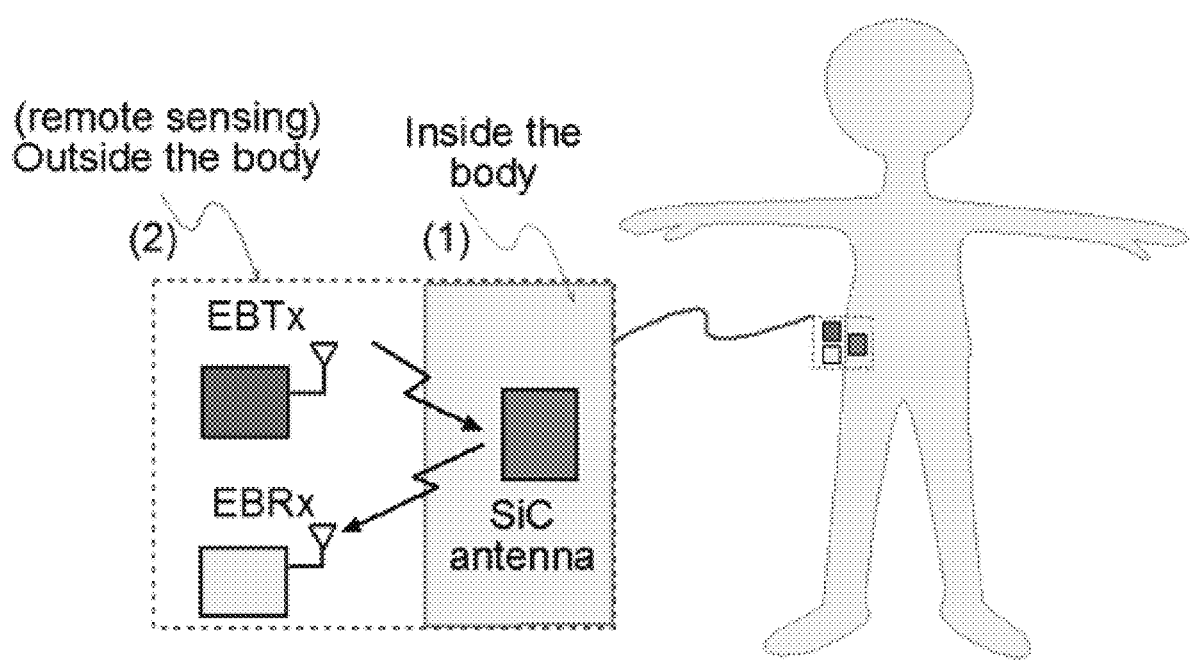
FIG. 2 depicts the primary components of the RFID-based, passive sensing continuous glucose monitoring system (PSCGM), displayed in their approximate locations. These components include two (2) external antennas and electronic circuitry for signal generation translation, and power control. Signals are sent from the external-to-the-body transmitting antenna (EBTx) towards the passive antenna and reflected back towards the external-to-the-body receiving antenna (EBRx). The internal, biocompatible passive SiC antenna is implanted within the body sub-dermally. Changes in sensor resonant frequency will then be measured by changes in received power as the transmitter frequency is swept over a frequency range equal to the anticipated change in glucose levels.

The system further includes an external device composed of two antennas (transmit and receive), power, and electronics to produce, transmit, and translate received signals into meaningful outputs. This device produces a radiofrequency (RF) signal from a transmitter, matched to the resonant frequency of the external transmitting antenna, which transmits the signal into the body towards the implanted antenna. The implanted antenna receives the signal and reflects it back out of the body, where it is captured by the external receiving antenna. The electronics then correlate changes in the revived RF signal to the patient's current blood sugar level. FIG. 2 illustrates these components of the PSCGM, along with the communications between the components.

Figure 3A:
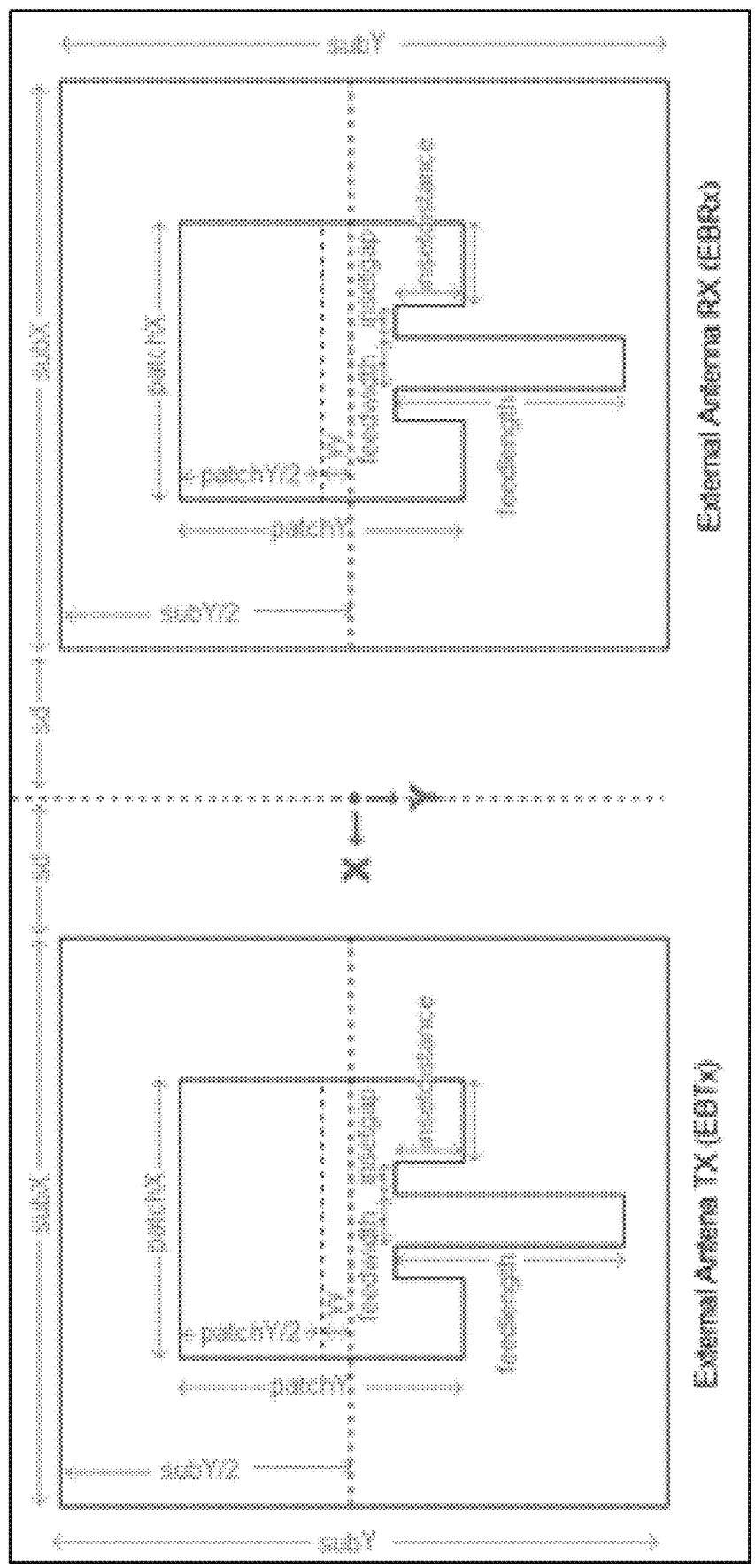
FIG. 3A is illustrations of the patch antennas which were made to the specifications shown in Table 1.
Figure 3B:
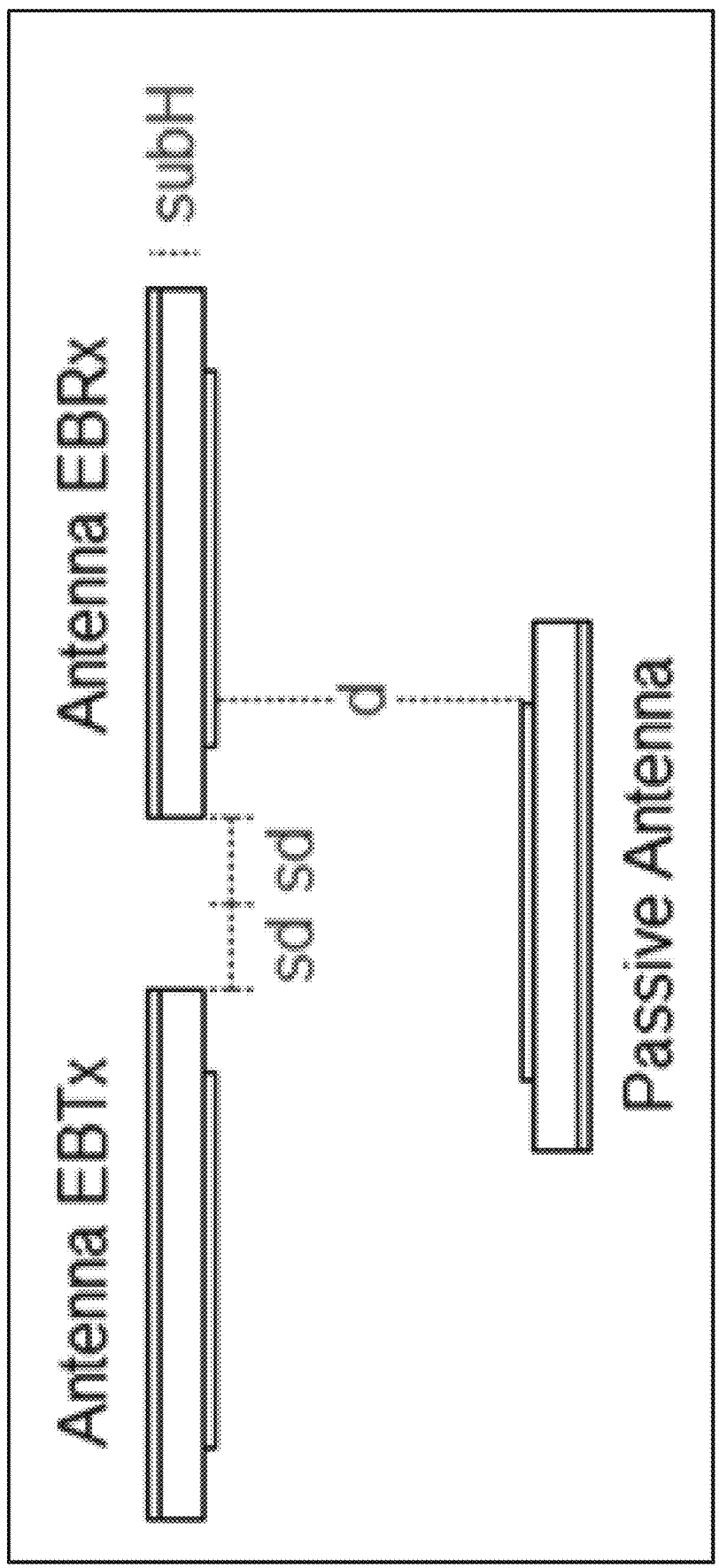
FIG. 3B depicts the positions of the antennas in regard to each other used in the verification of the principals described herein.

One of the major limitations facing this technological approach would be the attenuation of the original signal and its reflection as it passes through the physiological environment. To test this limitation and for proof of concept, three (3) 2.4 GHz (ISM band) patch antennas were constructed using COPPER DUROID 6010. The dimensions of the patch antennas are listed in Table 1, and their configurations can be seen in FIG. 3A. The antennas EBTx (external transmission antenna) and EBRx (external receiving antenna) were mounted adjacent to each other. The third antenna patch, acting as the passive sensor, was mounted directly towards EBTx and EBRx (FIG. 3B).

TABLE 1

| | | | |
|---|---|---|---|
| subX | 4.6 | cm | 4.6 cm |
| subY | 6.1 | cm | 6.1 cm |
| subH | 50 | cm | 50 mil |
| patchX | 2.59 | cm | 2.59 cm |
| patchY | 1.9 | cm | 1.9 cm |
| FeedWidth | 0.119 | cm | 0.119 cm |
| InsetGap | 0.06 | cm | 0.06 cm |
| InsetDistance | 0.69 | cm | 0.69 cm |
| FeedLength | 1.951 | cm | 1.951 cm |

Figure 4:
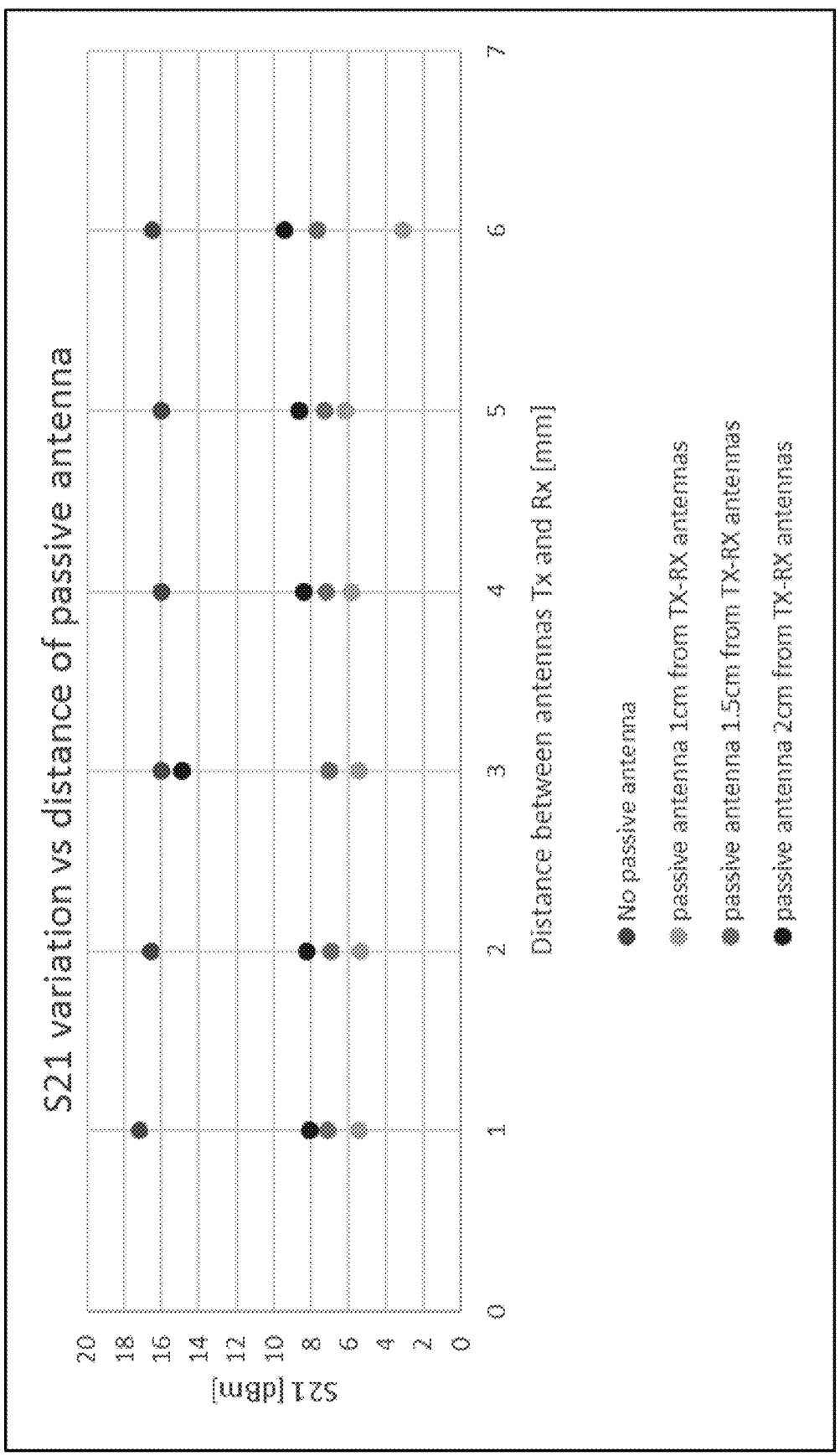
FIG. 4 depicts the $S_{21}$ power variation as distances between antennas were varied. Note that $S_{21}$ power is negative dBm.

Initially, the setup was simulated using ANSYS HFSS software. The distances between the EBTx and EBRx antennas, referred to in FIG. 3B as "sd", varied from about 1 mm to about 6 mm during simulation. The distance, referred to in FIG. 3B as "d", between the passive antenna and the EBTx/EBRx antennas were varied—about 1, 1.5, and 2 cm, and also with no passive antenna present. The results from this simulation, displayed in FIG. 4, shows a plot of $S_{21}$, representing the power received at antenna EBRx relative to the power transmitted from antenna EBTx. The x-axis represents the varying distances between the EBTx & EBRx antennas. With no passive antenna, $S_{21}$ is greater than −16 dB. It was found that as the distances between antennas EBTx and EBRx was decreased, the $S_{21}$ power measured also decreased.

Figure 5:
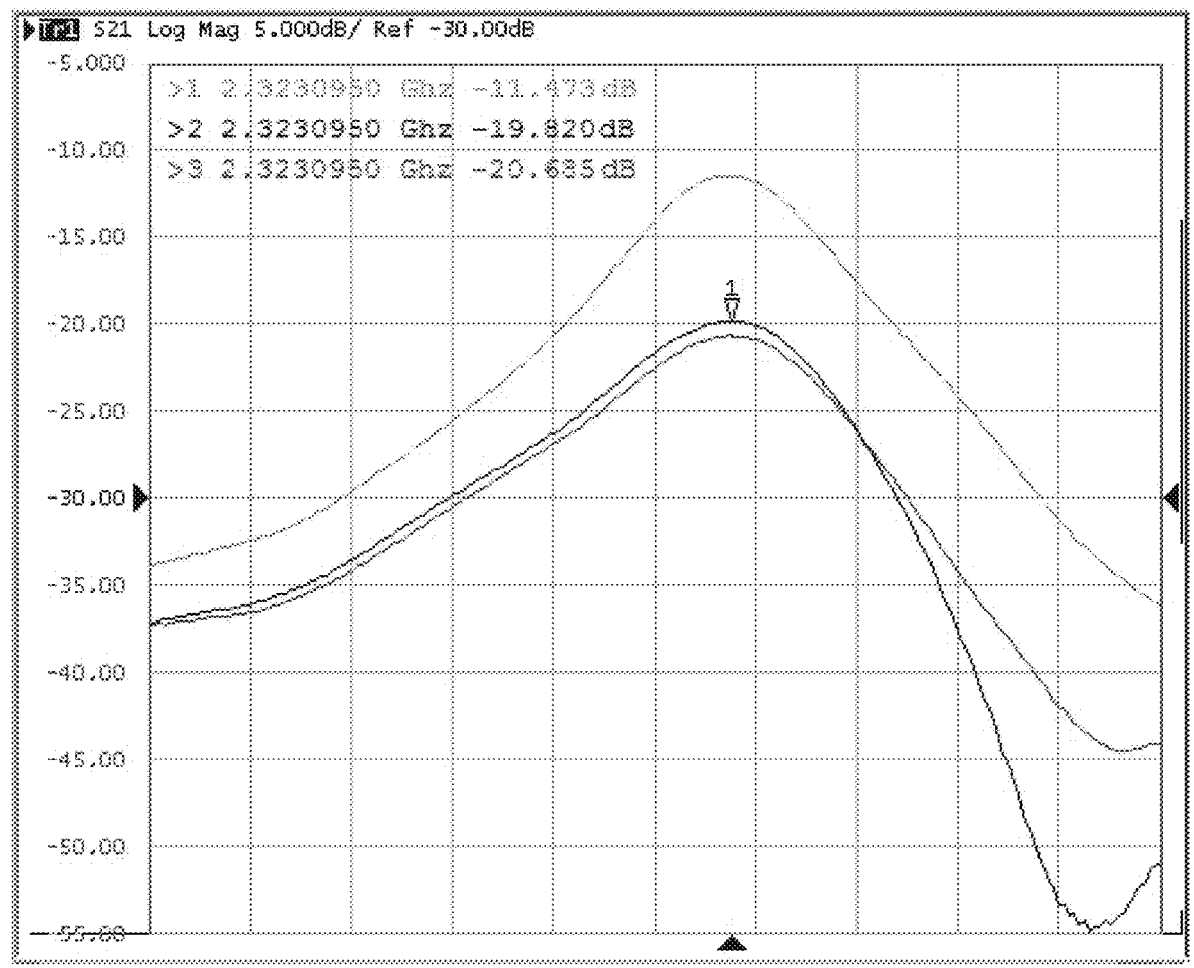
FIG. 5 is a graph of $S_{21}$ displaying the variations due to changes in glucose levels within FBA solutions. The green signal represents an empty dish; the red signal displays the signal due to the addition of FBA and w74 mg/dL glucose; the blue signal displays the change due to an increase in the glucose to 294 mg/dL.

An experimental trial was designed to verify the simulations, as well as evaluate the ability of the setup to detect changes in glucose. The antennas EBTx and EBRx were placed at a distance of about 3.1 cm from the passive antenna, which allowed the insertion into polystyrene-covered Petri dishes filled with animal fetal blood albumens (FBA). The dishes contained predetermined ratios of D-glucose. The antennas EBTX and EBRX were placed next to each other at a distance of about 0.4 mm from each other (i.e., approximately adjacent to each other). The EBRx and EBTx antennas were connected directly to the network analyzer in order to record variations of the parameters $S_{11}$ and $S_{21}$. These variations were then used to determine if the method could adequately detect changes in glucose levels. FIG. 5 shows $S_{21}$ displayed signal variations due to changes in glucose within the media. The change in glucose levels led to measurable changes in $S_{21}$ amplitudes.

Figure 6:
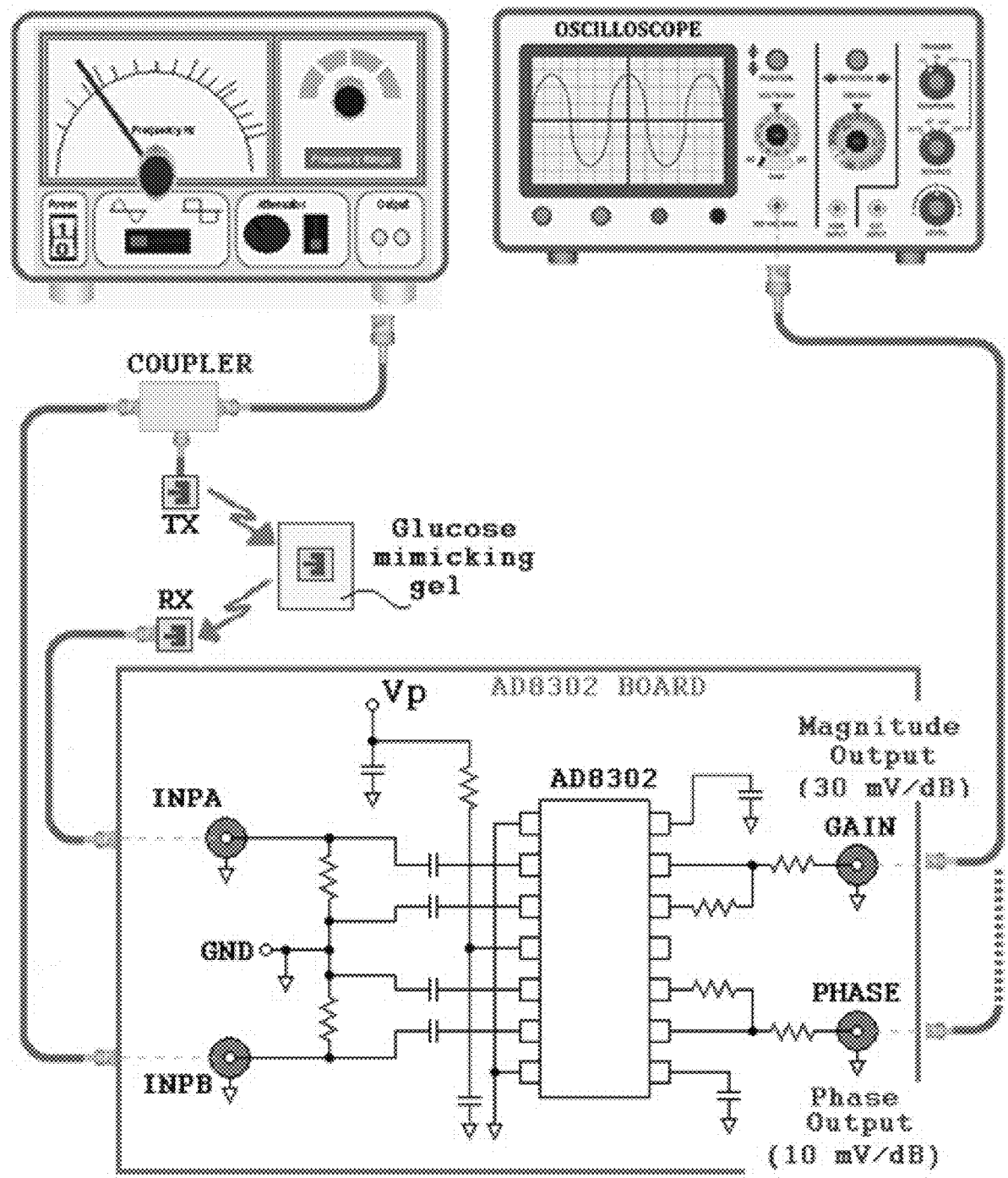
FIG. 6 depicts an experimental setup for the three antenna system. It is a schematic representation of connections of RFID sensor antennas to the AD8302 board. Note output gain (VMAG in text) and phase are shown on the right side of the figure.

The next aspect of the experimental trial was to vary the levels of glucose across physiological levels to solidify a functional relationship, thus verifying the operation of the sensor. The system was attached to an Analog Device AD8302, 2.7 GHz RF/IF integrated circuit. This IC is used to detect gain/loss and phase in numerous receive, transmit, and instrumentation applications. The ac-coupled input signals can range from −60 dBm to 0 dBm in a 50Ω system, from low frequencies up to about 2.7 GHz. The outputs provide an accurate measurement of either gain or loss over an approximate ±30 dB range scaled to about 30 mV/dB, and with phase over an approximate 0°-180° range scaled to about 10 mV/degree. By taking the difference of their outputs, a measurement of the magnitude ratio, or gain, between the two input signals is available. These signals may even be at different frequencies, allowing the measurement of conversion gain or loss. The experimental setup is illustrated in FIG. 6.

Recording of the sensor output was made using a digital oscilloscope set to about 500 mV per division. The baseline was established as the output measured from the EBTx antenna without connecting the receiving antenna on the board. The next recording was made after attaching the EBRx antenna, which led to a loss of about 1V at the output. The reflection (passive) antenna was then added, leading to a signal amplitude increase of about 125 mV and validated that the system was working properly. Ten (10) polystyrene Petri dishes filled with FBA varying in levels of dissolved glucose concentrations. The $S_{21}$ measured levels are displayed in FIG. 6. A linear relationship across the glucose concentration is shown through a line fit of the measured data.

Silicon Carbide

In certain embodiments, the combination of physical, chemical, and biological properties of SiC were exploited to develop a family of biomedical devices. The "smart" biomedical devices, according to certain embodiments of the current invention, are designed around 3C—SiC in combination with amorphous SiC (a-SiC) insulation. a-SiC insulation possesses a high dielectric K value, potentially enabling it to act not only as an excellent insulating coating but also as a hermetic casing for delicate silicon electronics. Further, 3C—SiC has shown excellent in vivo biocompatibility across multiple animal species [C. L. Frewin, C. Locke, L. Mariusso, E. J. Weeber, and S. E. Saddow, "Silicon Carbide Neural Implants: in vivo Neural Tissue Reaction," Neural Engineering (NER), 6th International IEEE/EMBS Conference on, pp. 661-664, 2013; S. Afroz, S. W. Thomas, G. Mumcu, and S. E. Saddow, "Implantable SiC based RF antenna biosensor for continuous glucose monitoring," in IEEE Sensors, Baltimore, Md. USA, 2013], and a-SiC, which has also shown excellent biocompatibility, performed well in clinical trials involving blood stents [C. Hehrlein, "Stent Passivation with Silicon Carbide as a Possible Alternative to Drug-eluting Stents—A Comprehensive Review of Pre-clinical and Clinical Results," Interventional Cardiology Review, vol. 4, pp. 60-63, 2009].

These two forms of SiC (3C and a-SiC) are shown to be beneficial for use in biomedical devices as they encompass a cost-effective processing approach, allowing for the synthesis of thin films in conjunction with cost effective materials, like silicon and polymers. This approach avoids the need to etch away expensive bulk hexagonal SiC substrates to construct micron sized, freestanding devices. The development of 3C—SiC and a-SiC for biomedical devices will be discussed herein, along with the development of SiC-based continuous glucose monitoring and implantable neural interface devices. SiC possesses a high level of biocompatibility, which is an extremely critical requirement for long-term implantable biomedical devices [S. E. Saddow, Ed., Silicon Carbide Biotechnology: A Biocompatible Semiconductor for Advanced Biomedical Devices and Applications. Amsterdam: Elsevier, 2011, p.ˆpp. Pages].

Figure 7:
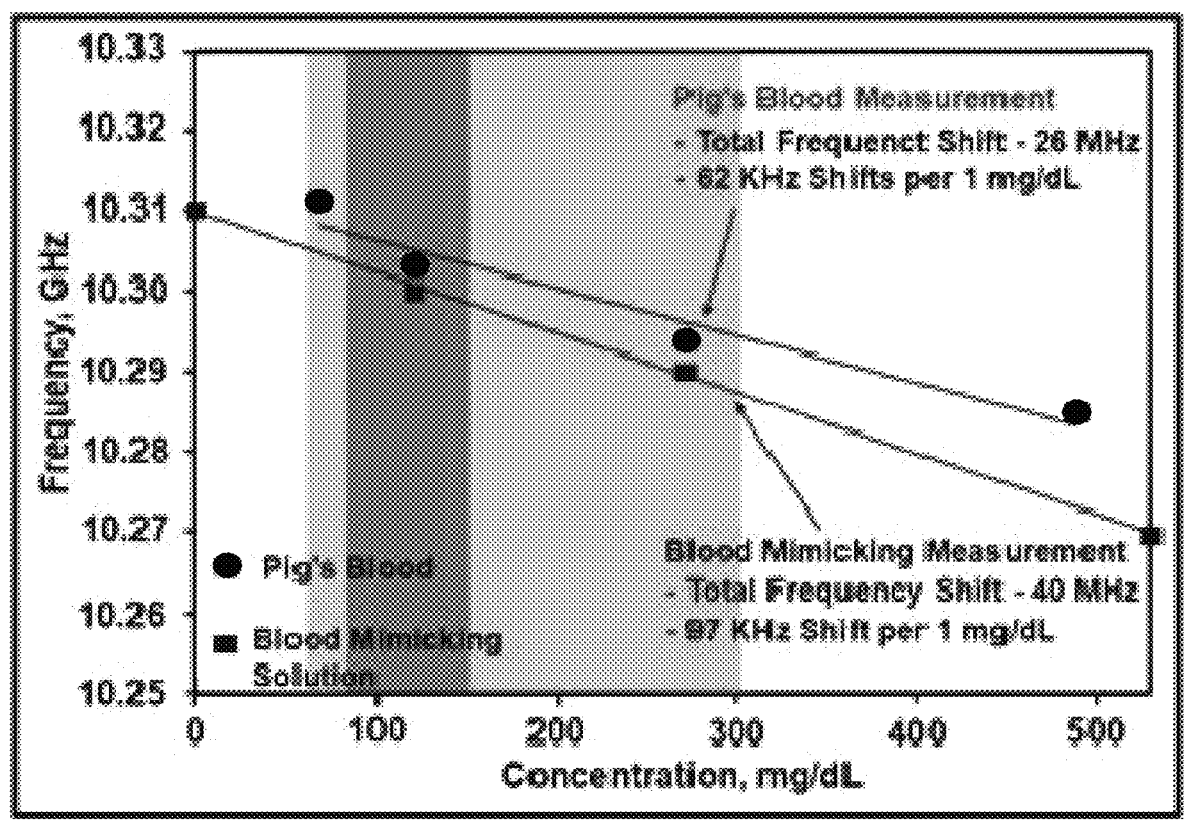
FIG. 7 depicts 4H—SiC sensor performance showing measurement of blood glucose levels with both synthetic and pig blood.
Figure 20A:
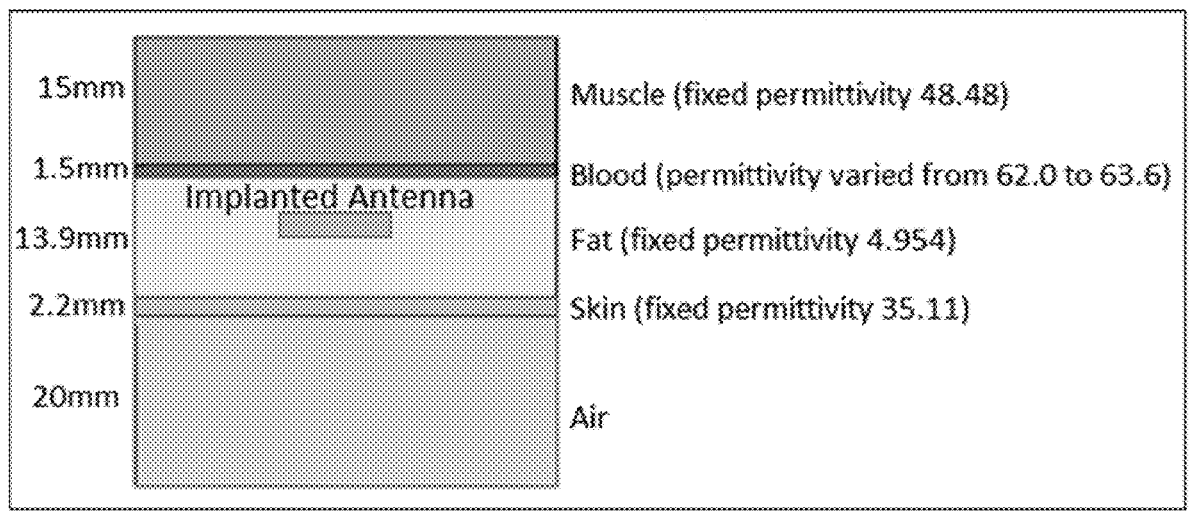
FIG. 20A is a schematic of a setup of a simulation in human tissue conducted via HFSS.
Figure 20B:
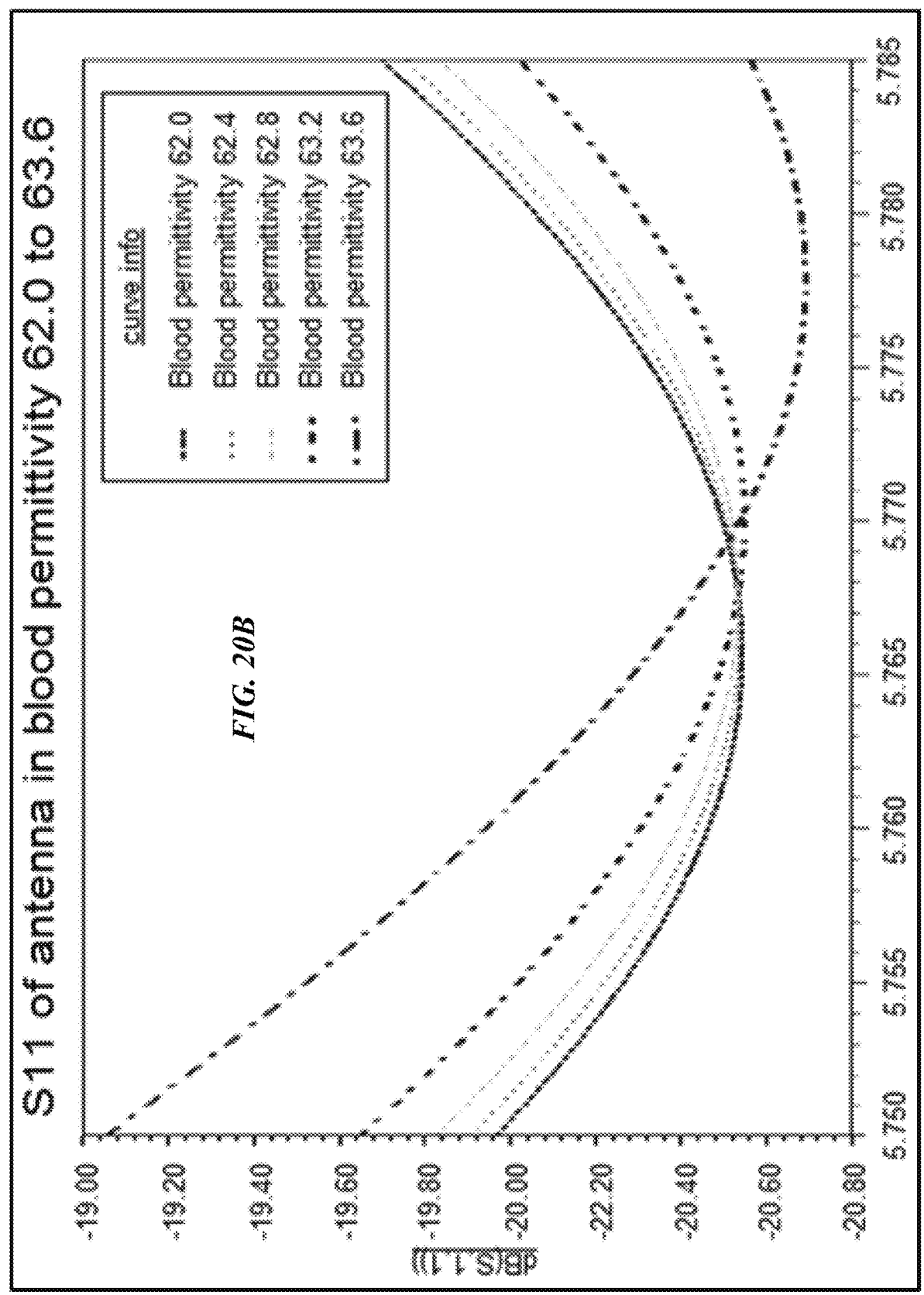
FIG. 20B is a graphical illustration depiting the results of the simulation of FIG. 20A.

The current inventors previously demonstrated in vitro efficacy of a continuous glucose sensor, employing a shift in RF frequency as a function of blood glucose level [S. Afroz, S. W. Thomas, G. Mumcu, and S. E. Saddow, "Implantable SiC based RF antenna biosensor for continuous glucose monitoring," in IEEE Sensors, Baltimore, Md. USA, 2013]. The change in glucose level manifests itself electrically as a change in the electrical permittivity of the blood. To test the sensor as a function of glucose level, measurements were performed using synthetic body fluid (SBF), which is electrically equivalent to blood plasma and pig blood; the result observed was a clinically useful change in frequency (see FIG. 7). Using a similar concept, a simulation of an antenna implanted in the fatty area of the human tissue was run in HFSS ANSYS using the model in FIG. 20A, set up with PML (perfectly matched layer) boundaries. The thicknesses and the permittivity values configured for the simulation were done based on the average adult human. The results of the simulations showed that for 500 mg/dL in blood glucose levels, variation simulated by varying the blood permittivity from 62 to 63.6 showed a total shift of resonant frequency of 12.3 MHz (see FIG. 20B).

Figure 8:
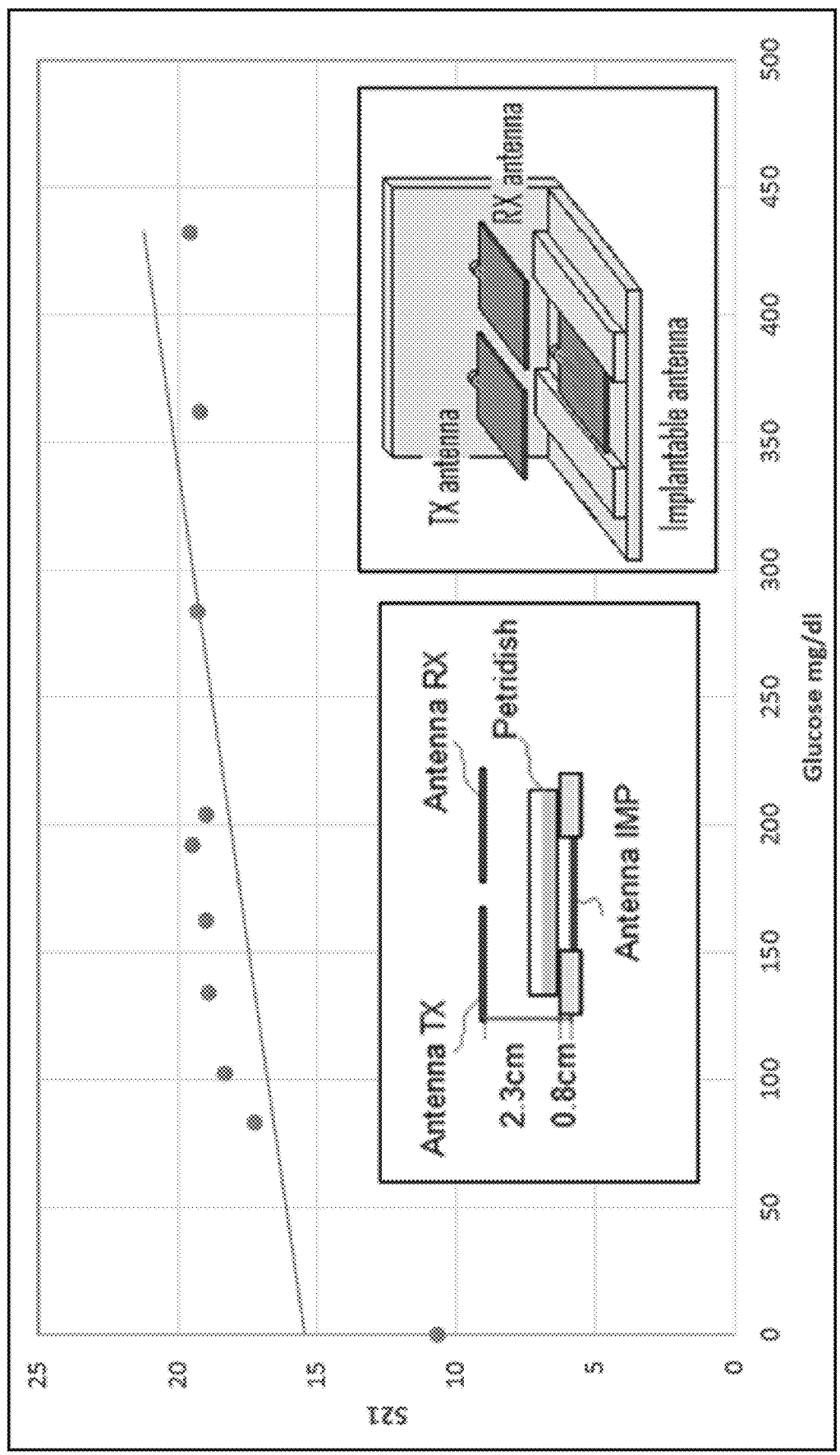
FIG. 8 depicts the testing setup and the $S_{21}$ levels of variation measured with changes in glucose concentration with FBA solution.

The glucose measurements were performed at 10 GHz, which is an RF band not normally used for biomedical devices. In addition, the device used an active, or powered, sensor to be powered in vivo, which can present challenges associated with incorporating a power source, such as thermal heating issues, etc. However, based on these results, it can be seen how CGM can be accomplished using a passive radiofrequency identification (RFID) type of approach. Briefly, RF frequency electromagnetic waves are transmitted to a passive antenna implanted in vivo. FIG. 8 shows the system configuration for this passive sensor strategy. The patch antenna for this configuration was redesigned for operations in the industrial, scientific, and medical (ISM) radio band (2.45 GHz center band), changing its dimensions from 11.5 mm×8.5 mm×0.37 mm to 2 61 mm×46 mm×1.27 mm. Clinically relevant levels of glucose were loaded into a blood mimicking solution, resulting in changes in the transmitted wave amplitude, leading $S_{21}$ amplitude measurements that are linked directly to glucose level (see FIG. 8). These measurements, for cost and ease of fabrication purposes, were made using standard copper RF boards, and a semi-insulating 4H—SiC antenna was fabricated to function as the passive implanted sensor.

SiC RF Antennas for In Vivo Continuous Glucose Monitoring and Wi-Fi Applications Discussed herein is the development of a bio- and hemocompatible glucose sensor based on the use of an RF antenna constructed using 4H—SiC. It was seen in a 30-day experiment that pig muscle showed no immune system response to the sensor, as well as variants in sensor materials (3C—SiC, a-SiC).

The ISM band at 2.45 GHz was chosen for this particular implementation due to its use for medical purposes and for its compromise between size and sensitivity. However, it can be understood that other frequency bands can be used as well, depending on use and feasibility. Other frequency bands include the Medical Implant Communication Services (MICS) at 402 to 405 MHz and the Wireless Medical Telemetry Service (WMTS) band between 608 to 614 MHz, 1395 to 1400 MHz, and 1427 to 1429 MHz.

Sensor Platform Development for the ISM Band (2.45 GHz)

The current sensor is an alternative for and an improvement over conventional CGM systems based on the remote sensing of glucose-related changes in an implanted SiC-based antenna sensor. The current inventors previously demonstrated that a 4H—SiC-based antenna operating in vitro at 10 GHz will experience a shift in resonant frequency as a function of change in glucose levels. A shift of 97 kHz and 67 kHz per 1 mg/dl change in blood glucose was observed in blood-mimicking liquid and pig blood, respectively. The antenna has been re-designed herein for the ISM band, which is a medical band allocated for biomedical devices, and tested in a platform design composed of two (2) additional antennas to enable remote sensing, where the antenna senses blood glucose changes using a similar mechanism to RFID. This RFID approach does not require contact with patient ISF, thus solving the short-time of use issue with present day implantable CGM sensors. The correlation between the external reflected signals with the variations of shift of the parameters of the implanted antenna were recorded and analyzed to determine patient glucose level in real time.

Figure 9A:
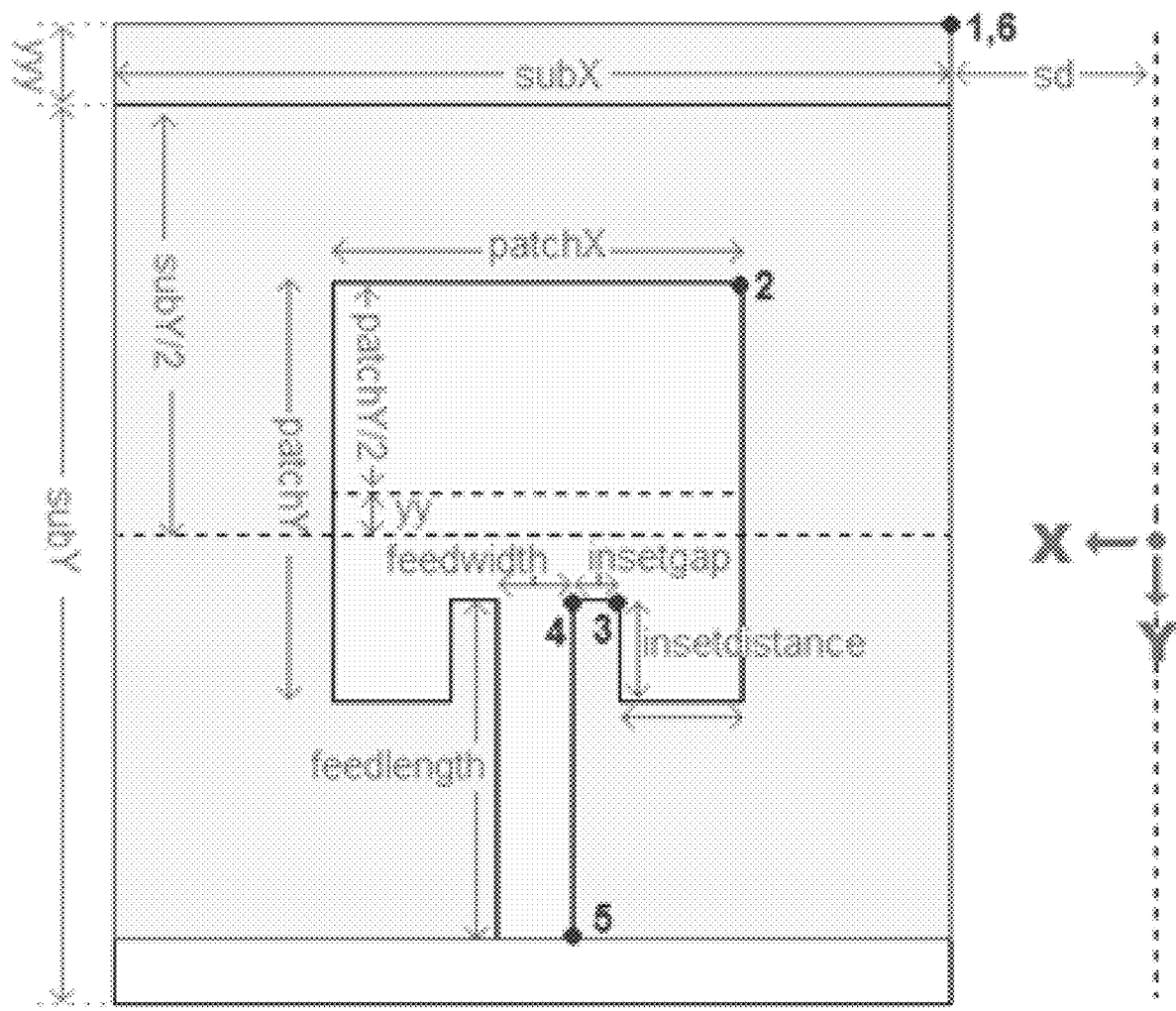
FIG. 9A depicts a band patch antenna showing antenna geometry.
Figure 10:
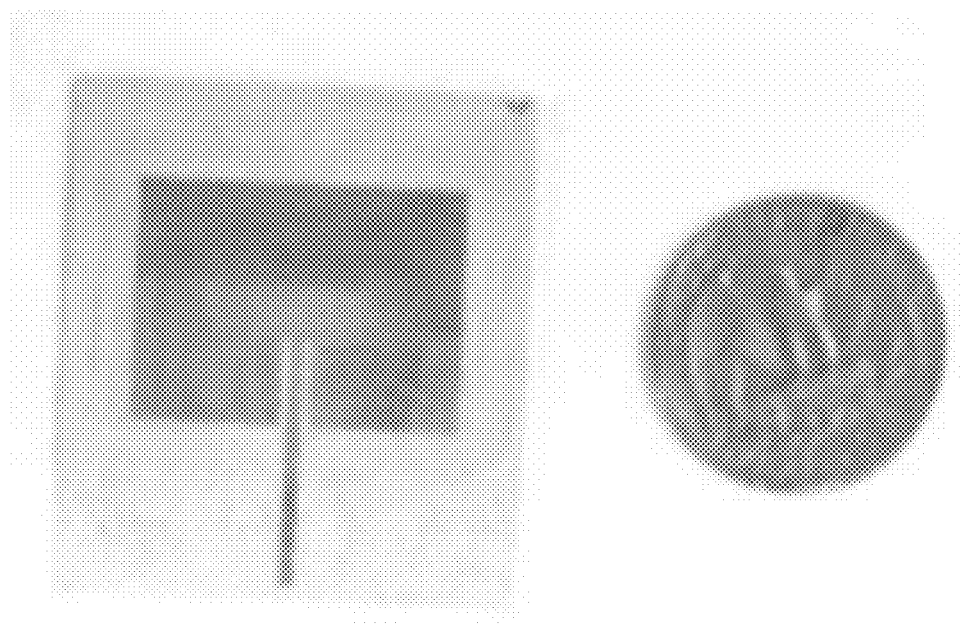
FIG. 10 is a photograph of IMS band microstrip patch antenna. Antenna substrate Rogers Duroid 6010, 50 mil thick. Dimensions shown in FIGS. 11A-11B.
Figure 11A:
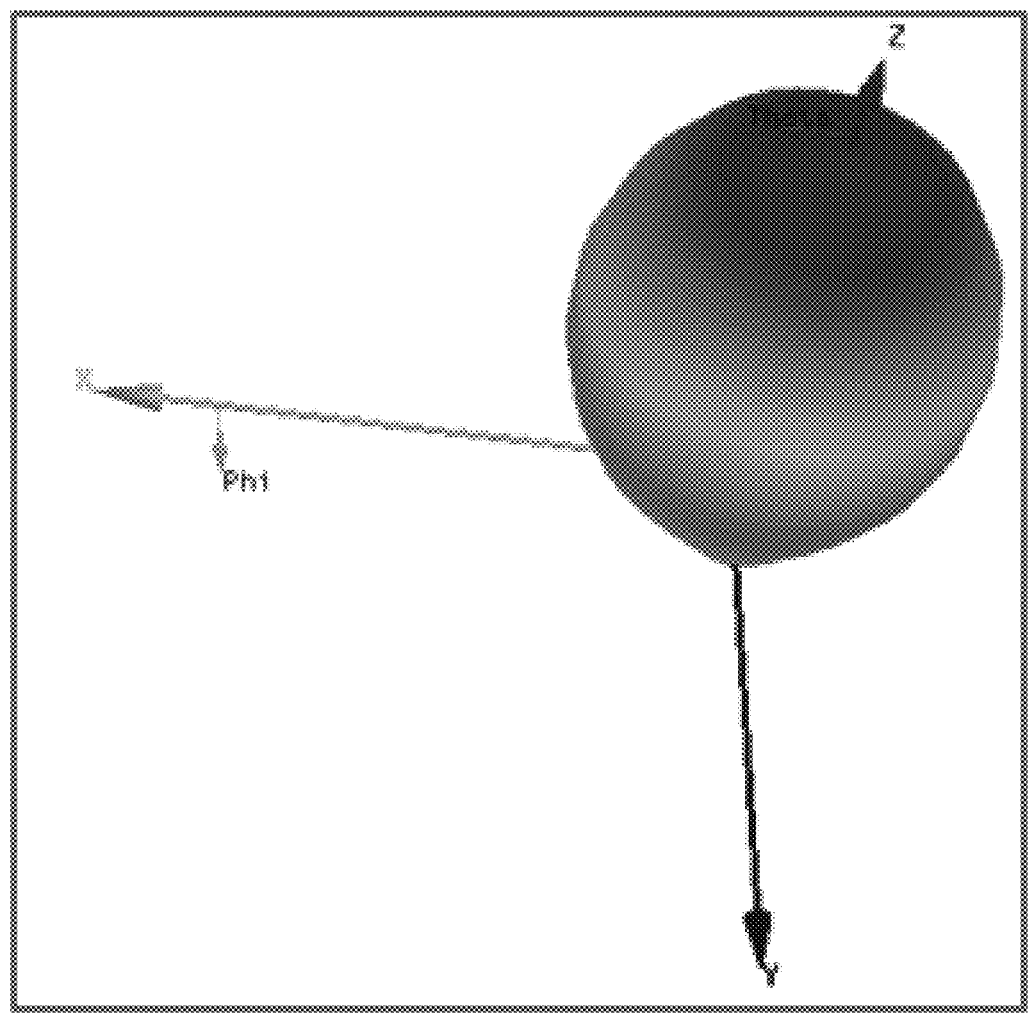
FIG. 11A depicts IMS band microstrip patch antenna simulated radiation pattern.
Figure 11B:
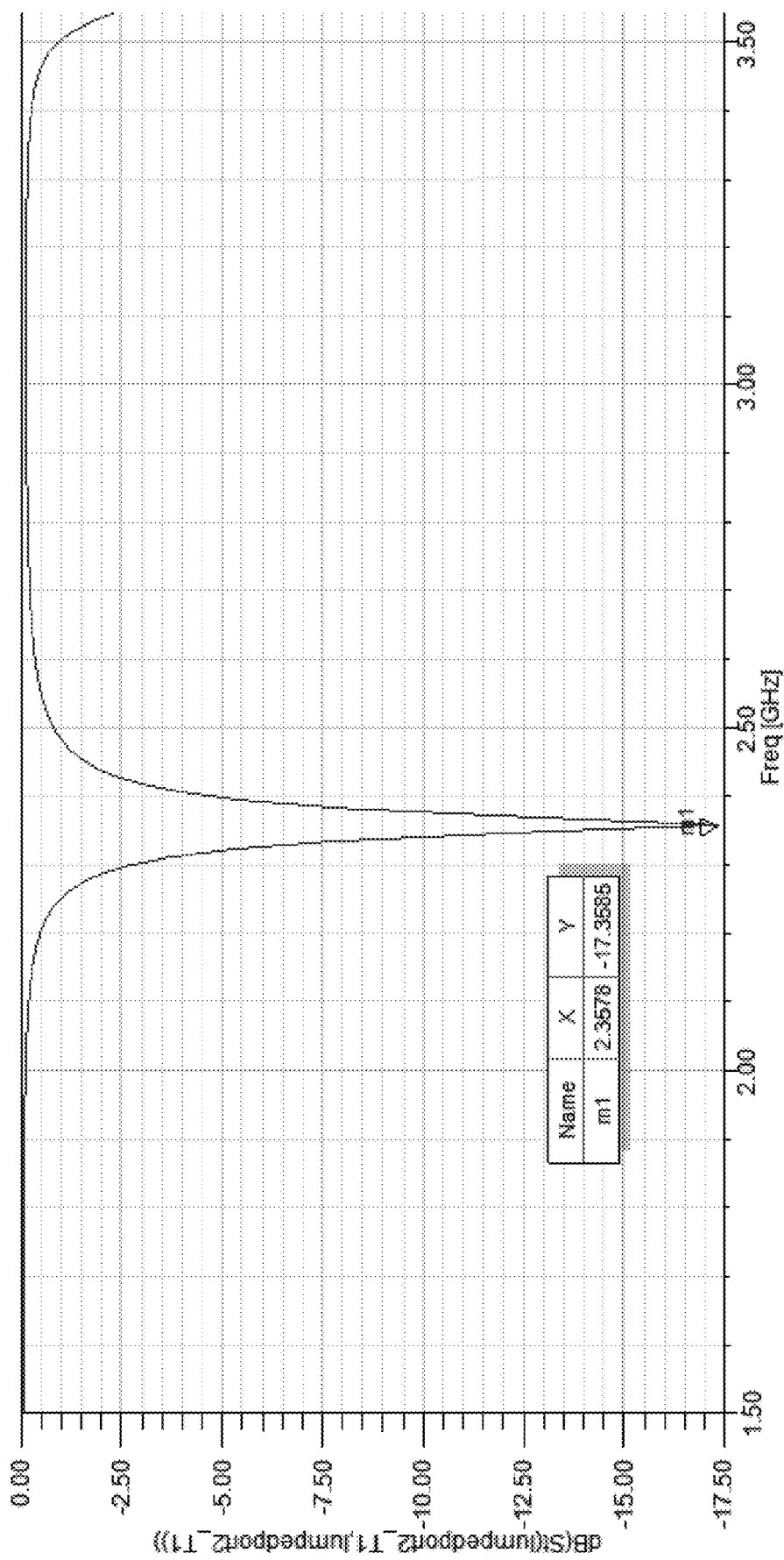
FIG. 11B depicts IMS band microstrip patch antenna simulated $S_{11}$ response.

As a preliminary trial, the current antenna was designed using Roger's Duroid 6010™ as the substrate with a thickness of 50 mil. FIG. 9A shows the antenna patch geometry, with the corresponding dimensions listed in FIG. 9B. A photograph of the fabricated antenna is showed in FIG. 10, also depicting relative size. This was simulated using ANSYS HFS resulting in the simulation beam profile shown in FIG. 11A, and the $S_{11}$ response shown in FIG. 11B.

RFID Sensing Platform for CGM Using SiC RF Antenna

An object of the current invention is to provide an implantable SiC RF antenna for a long-term CGM sensor platform, which can remotely detect variations in glucose levels as follows. An external-to-the-body transmitter (EBTx) transmits a variable frequency signal towards the implanted sensor (SiC patch antenna), which, in turn, reflects the signal. An external-to-the-body receiver (EBRx) receives the reflected signal (see again FIG. 2). Changes in the glucose levels that surround the implanted antenna will result in a variation of its resonant frequency as was previously demonstrated by the current inventors at 10 GHz. The power received at the EBRx will change directly in relationship to the variations of the resonant frequency of the implanted antenna, and thus amplitude changes will be an indirect, but accurate, measurement of the patient's glucose level. The sensor platform is designed to sweep the EBTx signal frequency in order to detect the variation of power over the range of frequencies used to identify the glucose level of the patient.

Figure 12:
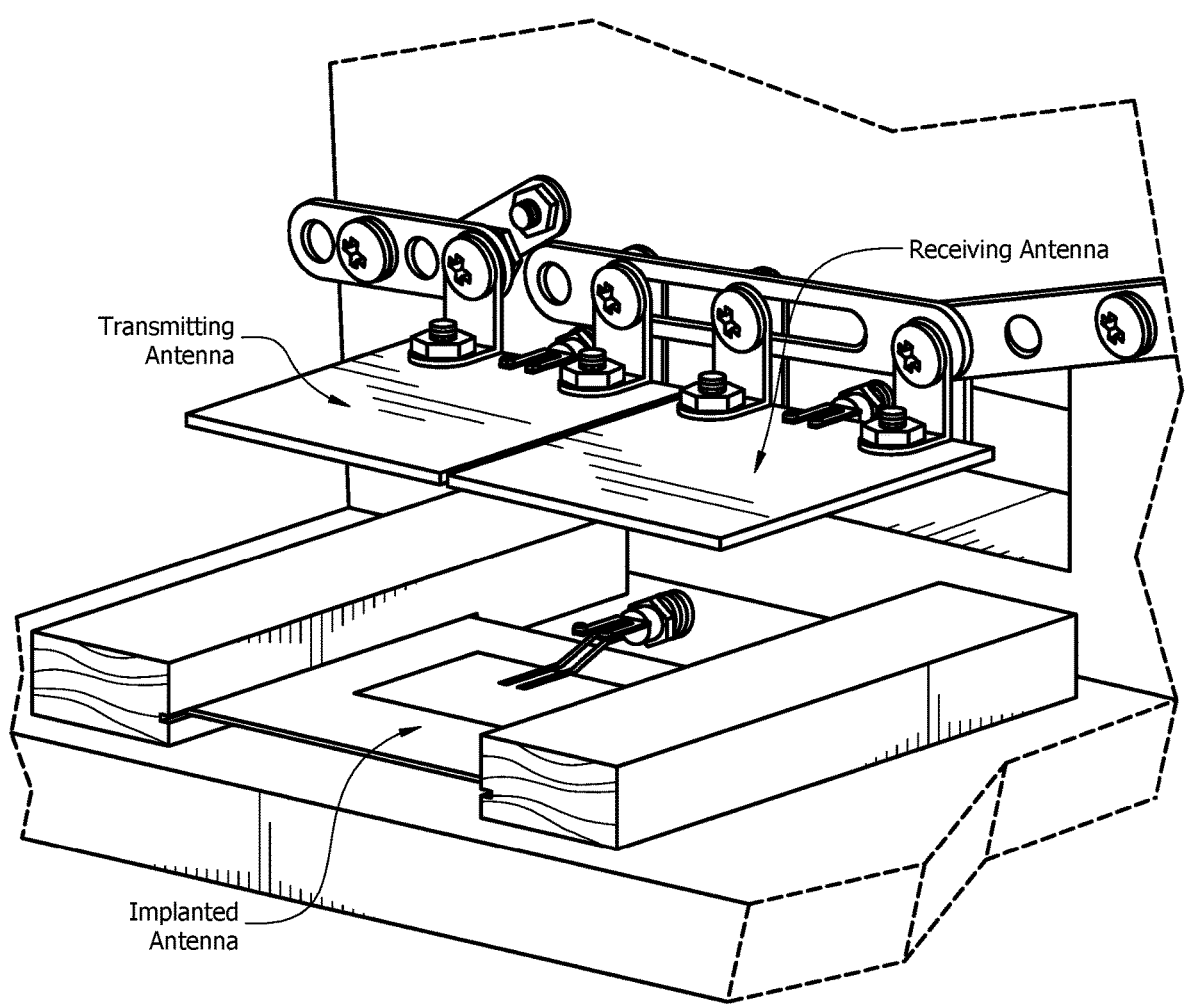
FIG. 12 depicts RFID detection RF front end showing the antenna location for the preliminary experimental trial. Blood mimicking liquid or pig blood will then be placed on the wooden platform above the Antenna IMP (not shown) so that changes in synthetic glucose level can be measured. The antenna to IMP height is 26 mm. Note EBTx and EBRx antennas facing down with the integral ground plane visible.

In the first phase of the trials, three antennas were constructed. Two of the antennas (EBTx/EBRx antennas) were connected in close proximity to each other, facing a third antenna (implanted antenna), as shown in FIG. 12.

Figure 13:
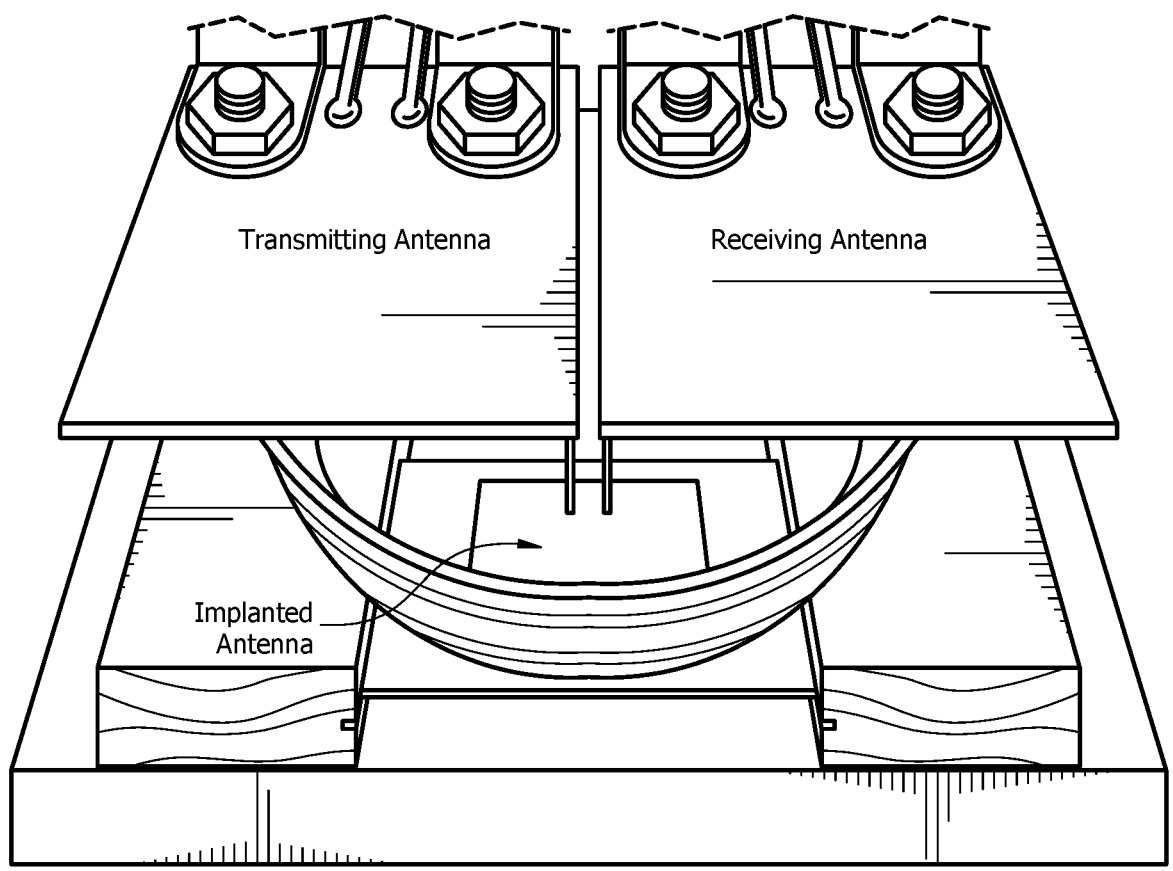
FIG. 13 depicts a Petri dish inserted between EBTx/EBRx antennas and IMP antenna. Spacing X mm. Petri dish contains FBA with varying concentrations of D-glucose and the RFID sensing mechanism was verified using this setup.

The setup, also shown in FIG. 13, allowed a Petri dish to be inserted at a fixed distance of about nine (9) mm between the EBTx/EBRx antennas and the IMP antenna (i.e., the implanted antenna). The Petri dish, as shown in FIG. 13, was filled with animal fetal blood albumens (FBA) combined in each test with set ratios of calculated D-glucose. The proportion of glucose in the FBA was both calculated and measured using the commercial glucose meter TRU-ETRACK.

Figure 14A:
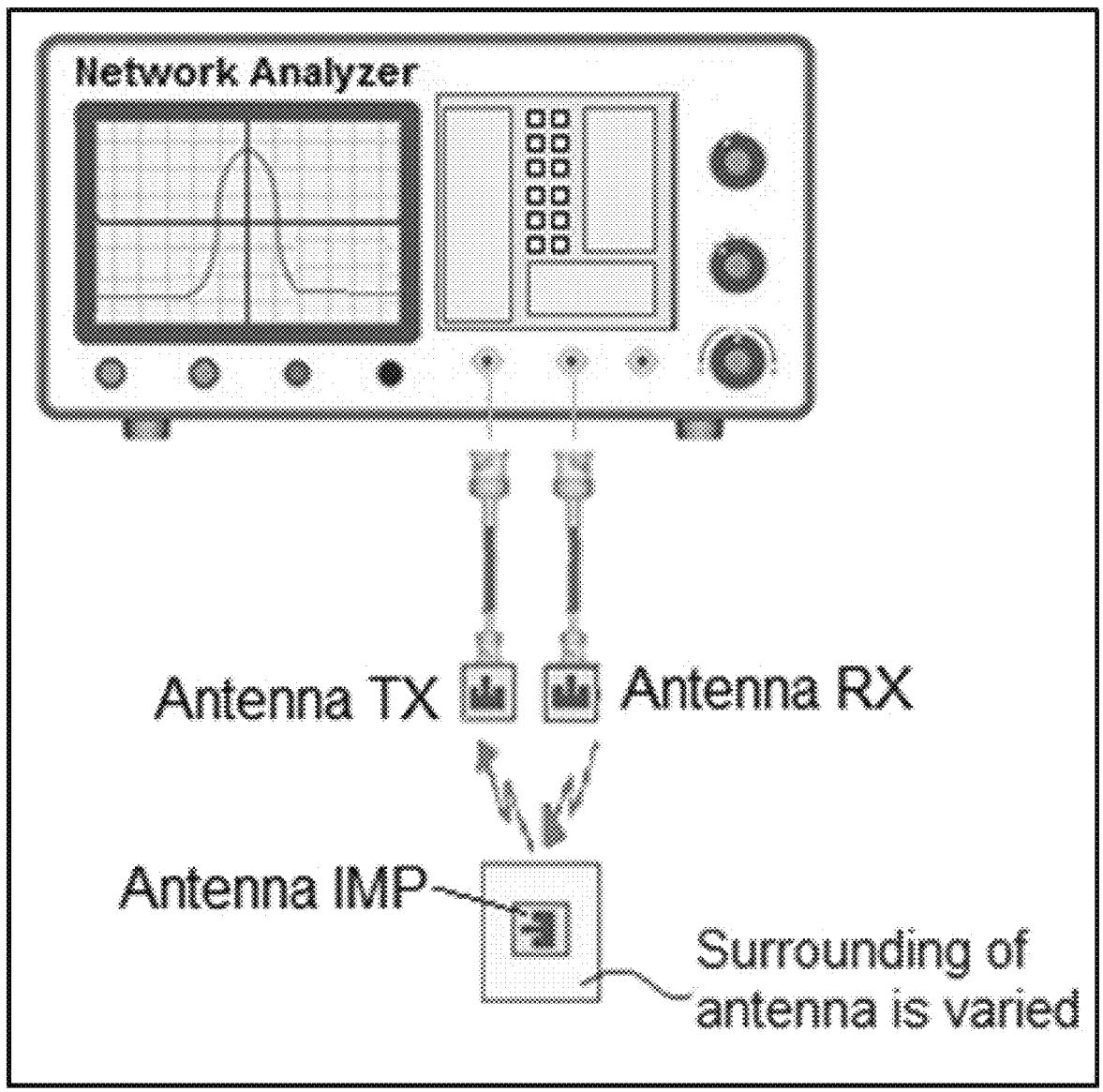
FIG. 14A depicts the RFID sensor showing antenna connections to the network analyzer used to obtain $S_{11}$ and $S_{21}$ as a function of glucose concentration.
Figure 14B:
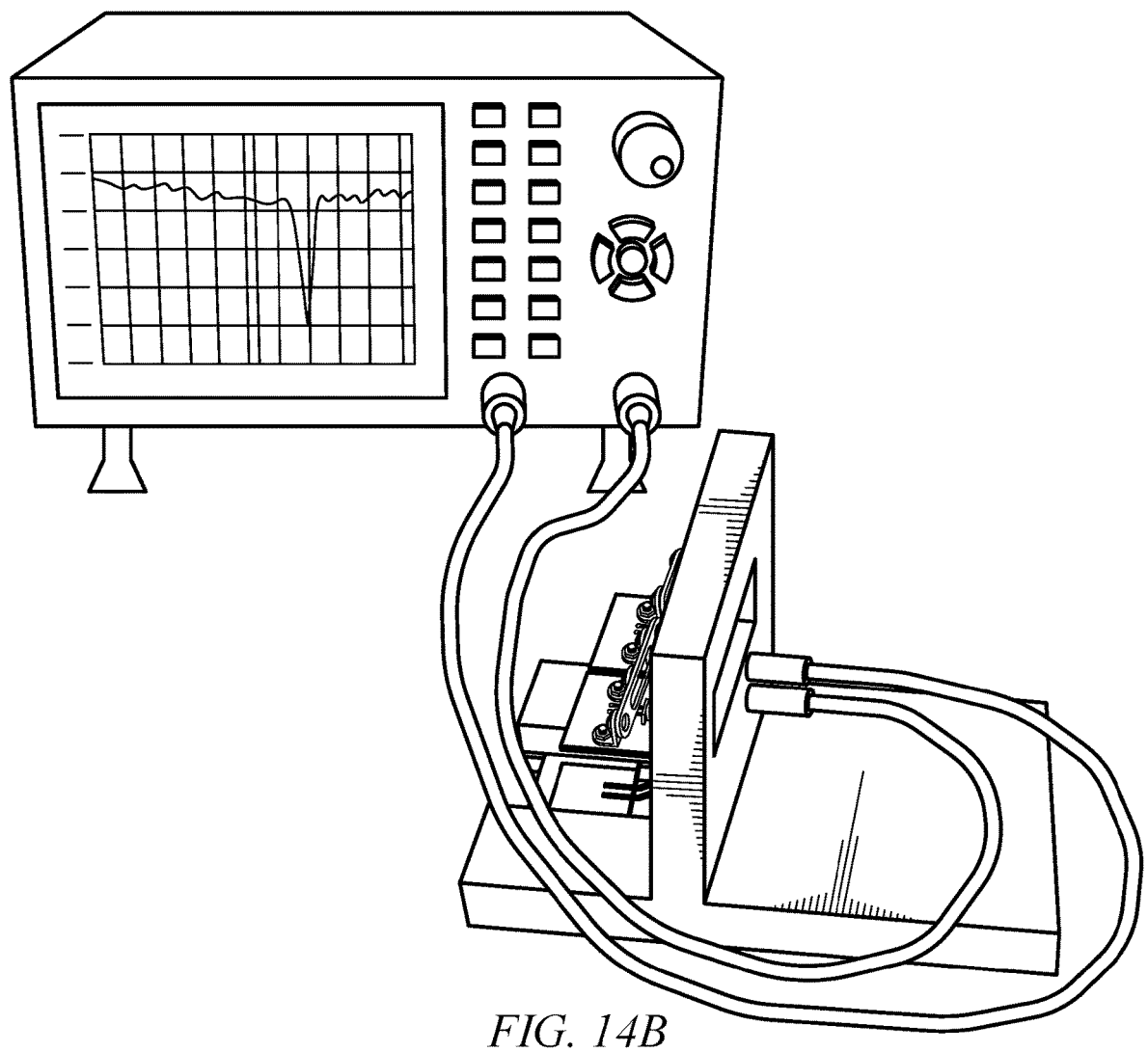
FIG. 14B is a photograph of RFID sensor under test.

During the first set of the RFID sensor trials, the EBRx and EBTx antennas were connected directly to the network analyzer in order to record the variations of the parameters $S_{11}$ and $S_{21}$ of the antennas as a function of the glucose levels of the FBA in the Petri dish. FIG. 14A shows a schematic representation of this setup, while FIG. 14B shows a photograph during an $S_{11}$ measurement.

The second phase of the RFID sensor trials included connecting the antenna to the AD8302. This analog device is measures gain/loss and phase in numerous receive, transmit, and instrumentation applications and can operate from low frequencies up to about 2.7 GHz. The AD8302 board was connected to the RFID (see again FIG. 5).

Recording of the sensor output VMAG was made using a digital oscilloscope. The oscilloscope was set to 500 mV per division. The first test was performed by recording the output without connecting the receiving antenna on the board and then by adding the receiving antenna. A value greater than 1V of difference was observed. The test was the continued by comparing the results of having no reflecting antenna (in open space) and the results of having a reflecting antenna. Adding the reflecting antenna resulted in a received signal amplitude increase of ~125 mV in VMAG which validated the RFID RF setup. Finally, the test was repeated with a blood glucose concentration of 100 mg/dL and 580 mg/dL—an easily measured variation in output voltage from the AD8302 board of approximately 3 mV was observed.

Ultimately, the variations of the glucose levels that surrounded the implanted antenna resulted in variations of its resonant frequency. The power received at the EBRx changed directly in relationship to the variations of the resonant frequency of the implanted antenna, and thus be an indirect measurement of the glucose levels. The process of the sensor platform included sweeping the sending signal frequency of the EBTx in order to detect the variation of power over the range of frequencies used to identify the glucose level of the patient.

In summary, this study shows that SiC RF technology has the potential to be used as glucose sensor to monitor patient blood glucose levels in real-time. This claim is predicated on the in vitro and in vivo) data that shows that SiC is biocompatible. In addition, these results can be transferred to various health care systems in the future, especially as a Wi-Fi node for the emerging biosensor/biosensor system market. This technology can provide an increase in the understanding of bio sensing/detecting and continuous diagnostic feedback and can deliver a platform for system integration of implantable Wi-Fi devices using SiC RF antennas. The implanted antenna can remain in the body for years, and the external antennas can be externally, outside the body, connected to an electronic circuitry to display the glucose levels real time, without the need for continuous blood glucose measurements via finger pricks which is known to be both painful and unreliable.

EXAMPLE

It is an object of this study to provide a sensor platform for the CGM to be able to display variations of the glucose levels outside the body that could give reliable results in frequencies suitable for medical band. The blood glucose levels that surround the antenna changes the resonant frequency at which the antenna operates. This was sensed remotely by sending a signal from the EBTx towards the implanted antenna, which reflected the signal towards the EBRx. The power level of reception of the signal at the EBRx depends on the frequency being sent by the EBTx as well as the level of glucose inside the body. The overall process consists of sending a signal from the EBTx at different frequencies and processing the information of the power levels received for each of those frequencies at the EBRx in order to find a correspondence to the glucose levels. At the end, a mathematical relationship between the glucose level and the resonant frequency was determined, and the glucose level along with the transmitting frequency in relationship with the power reception of the receiving frequency wave determined, along with an overall relationship among all parameters. Based on this relationship, the sensor platform can be configured.

The sensor platform includes the EBTx block that transmits a signal at different frequencies, the implanted sensor that receives and reflects the signal, and the EBRx block that receives the reflected signal (see FIG. 2). The EBTx block is formed of a low power microcontroller (e.g., MICROCHIP TECHNOLOGY PIC16F720), a direct digital synthesis (DDS) IC (e.g., ANALOG DEVICES AD9915, capable of generating frequencies up to 1 GHz), a transmitting antenna, and a battery for the power supply. An alternative for generating frequencies is using a phase-locked loop (PLL) with integrated voltage control oscillator (VCO) (e.g., MAXIM INTEGRATED MAX2870, capable of generating frequencies from 23.5 MHz to 6.0 GHz), or other suitable alternatives. The microcontroller controls the frequencies and times of the sinewave signals that are generated by the DDS IC. Specifically, the microcontroller controls the frequency sweep that is transmitted by the EBTx and processes the received signal from the EBRx.

Figure 15:
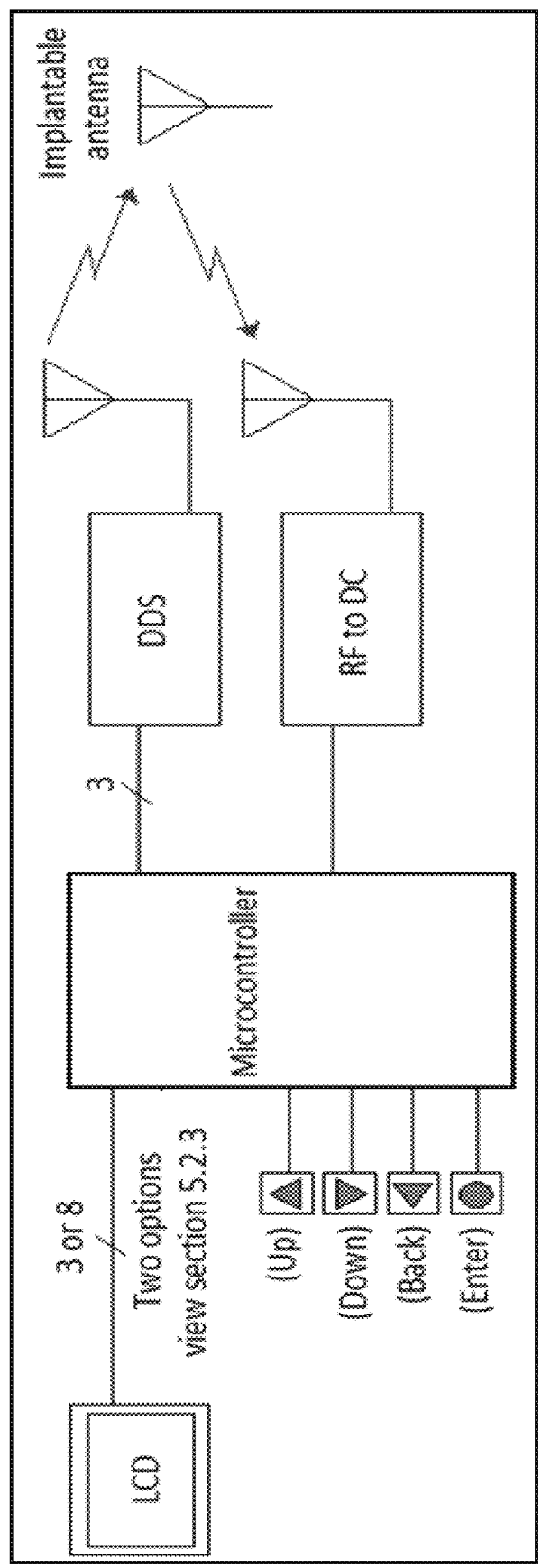
FIG. 15 is a block diagram depicting components of an embodiment of the sensor platform discussed herein.

The EBRx is formed of the same microcontroller and same battery supply, an RF-to-DC converter (including an RF power detector, e.g., TEXAS INSTRUMENTS LMH2121), an LCD for display (e.g., SHARP MICROELECTRONICS LS010B7DH01, HITACHI HD4478U) with serial interface, and a 4 push-button keyboard to control subsystem options. The RF-to-DC converter receives the reflected signal and converts it to a digital value that, in turn, can be sent to the microcontroller. The microcontroller stores the information in its memory, processes the information, and displays the corresponding glucose level on the LCD. The microcontroller communicates with a controller input (e.g., four-input push-button keyboard) to allow options of calibration, storing, history, and default value restore. A block diagram displaying the general parts of this sensor platform is displayed in FIG. 15.

Figure 16:
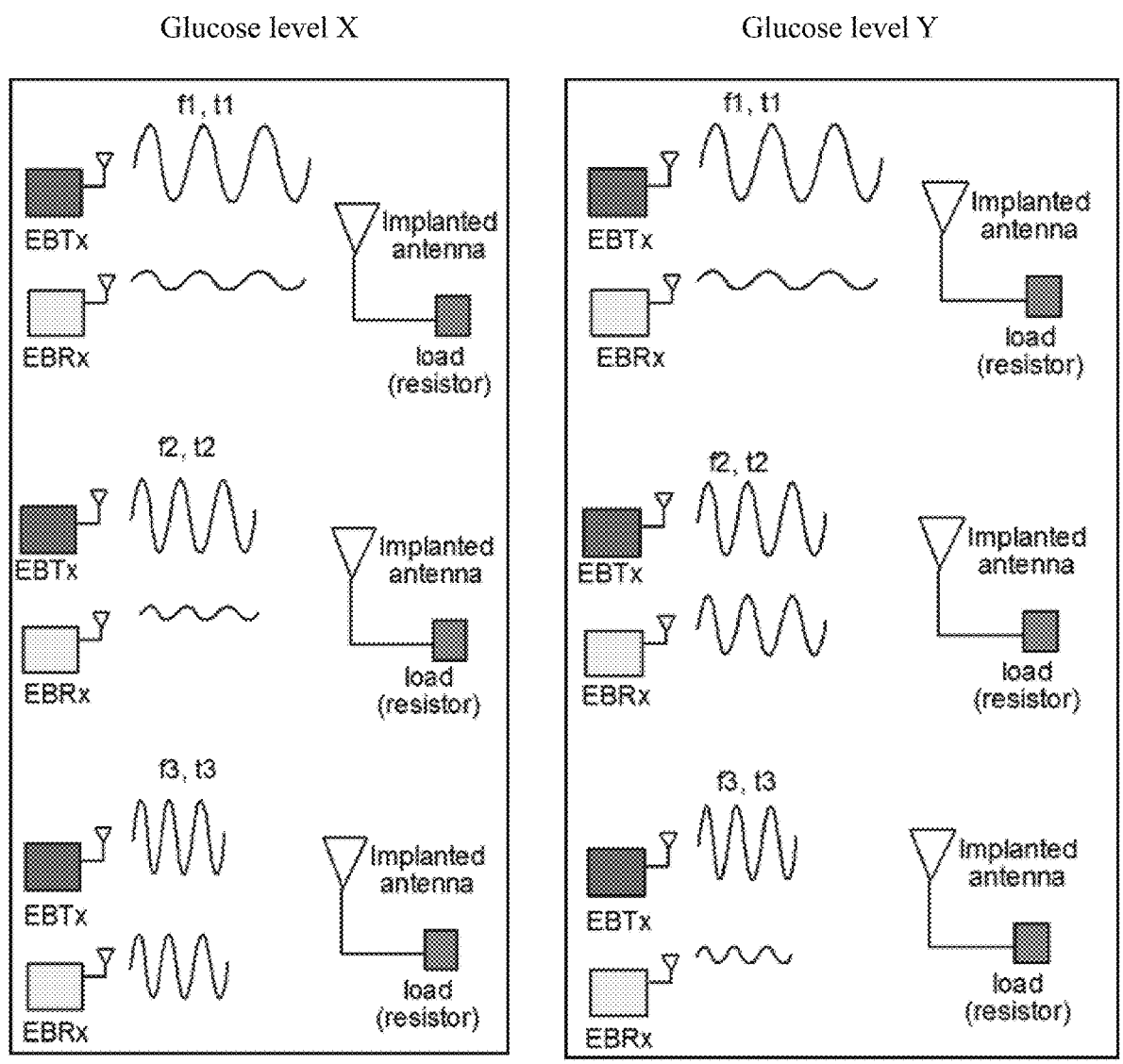
FIG. 16 depicts the concept of reflective signal depending on glucose level and frequency.

In method, the variation antenna resonant frequency is related to the glucose level that surrounds the antenna. FIG. 16 shows a visual concept of two cases, X and Y, where the implanted antenna is surrounded by medium glucose levels X and Y. In both cases, frequencies 1, 2, and 3 are sent to the implanted antenna at times 1, 2, and 3. For glucose level X, frequency 3 has a higher reflected signal than in frequencies 1 and 2, while for glucose level Y, for those same frequencies, frequency 2 has a higher reflected signal than in frequencies 1 and 3.

In order to determine the correlation of the received signal and the frequency and glucose level, initial manual tests should be conducted, as previously discussed. Once the range of frequencies of operation and correlation between glucose levels and reflected signal in the EBRx are determined, these frequencies are stored in the memory inside the microcontroller (see FIG. 17). The data address memory 0 contains the number of total different frequencies that are to be evaluated for each glucose level. A second section of the data memory can be allocated to store the data of the glucose signal received, variable G_signal (see FIG. 18).

Figure 19A:
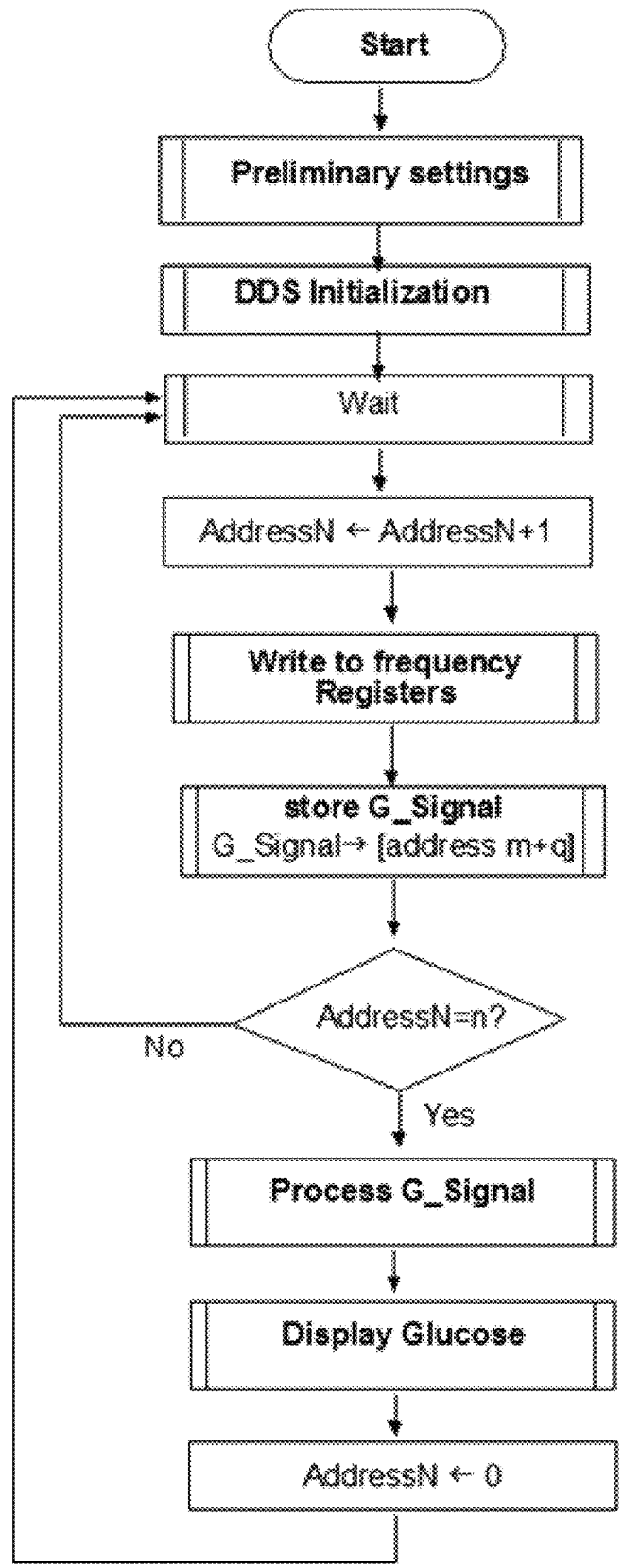
FIG. 19A is a flow diagram of the microcontroller main program.
Figure 19B:
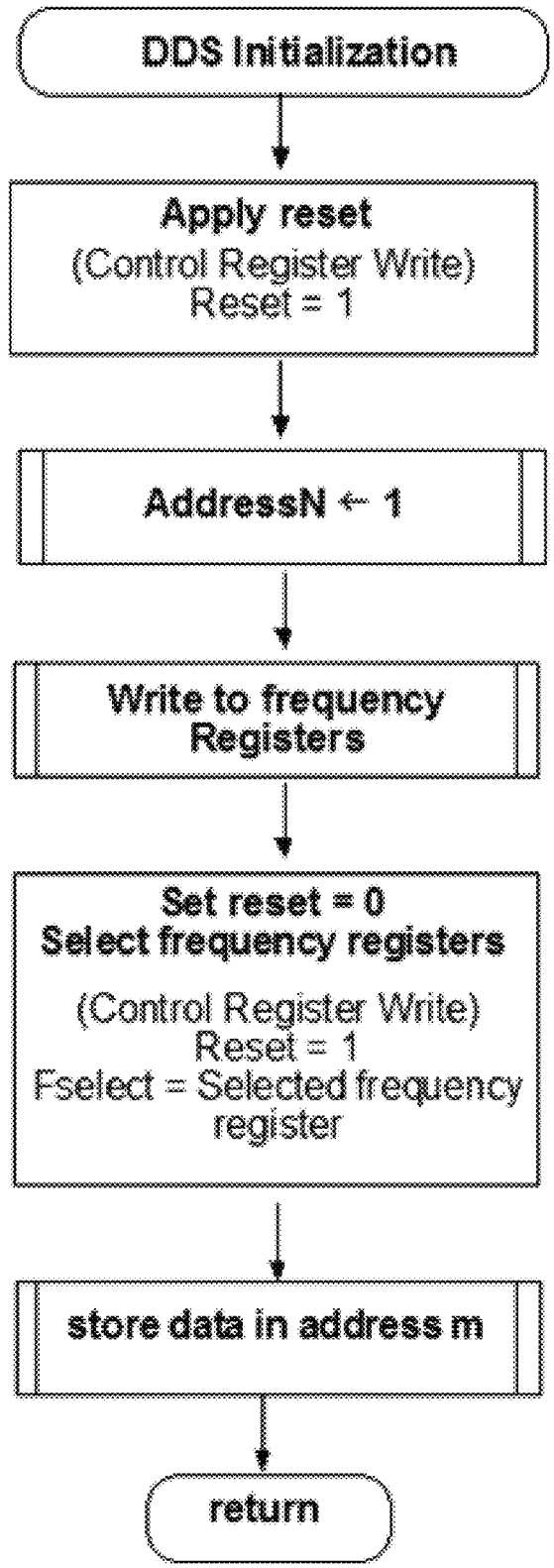
FIG. 19B is a flow diagram of the DDS initialization subroutine.
Figure 19C:
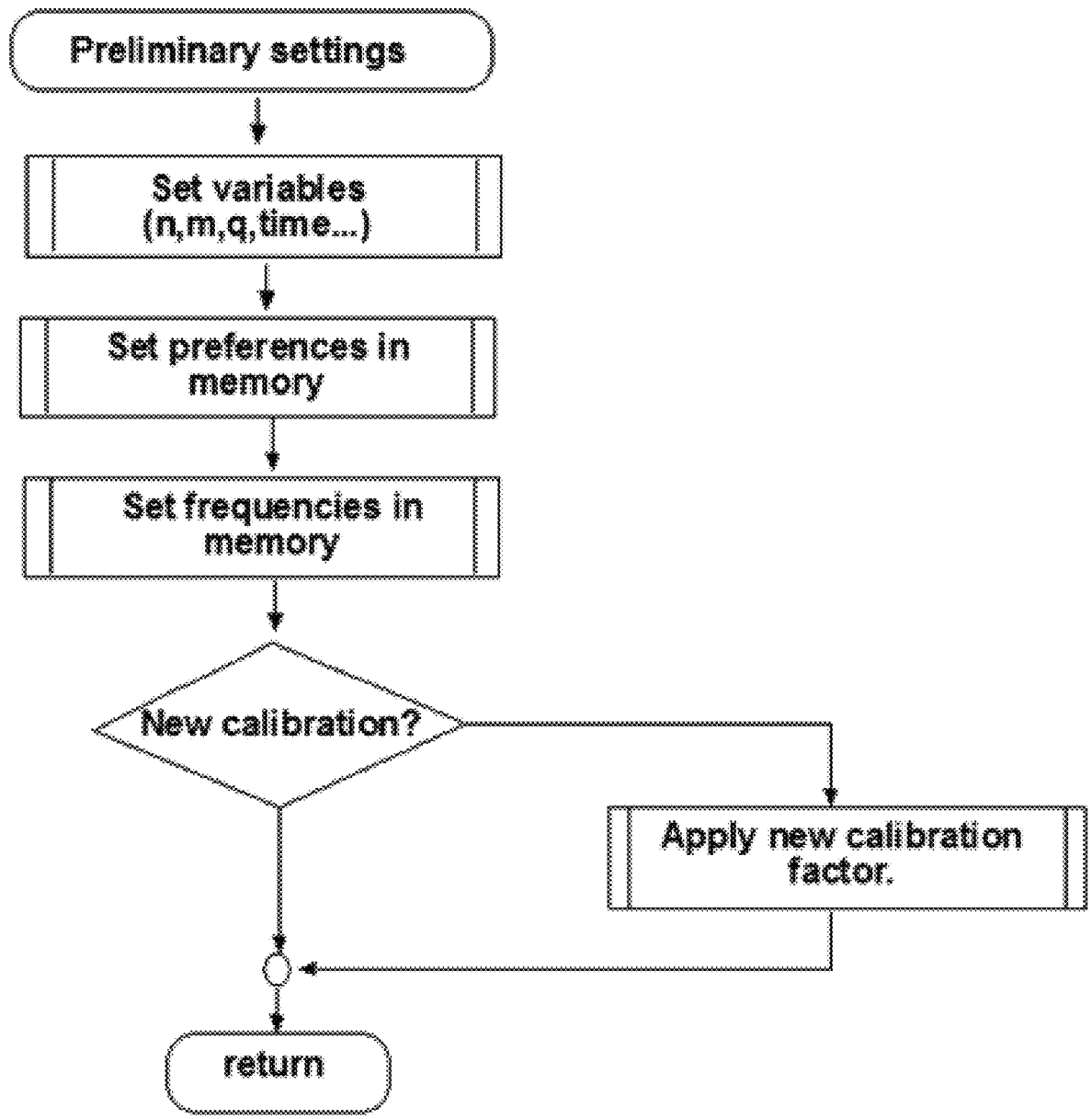
FIG. 19C is a flow diagram of the preliminary settings subroutine.
Figure 19D:
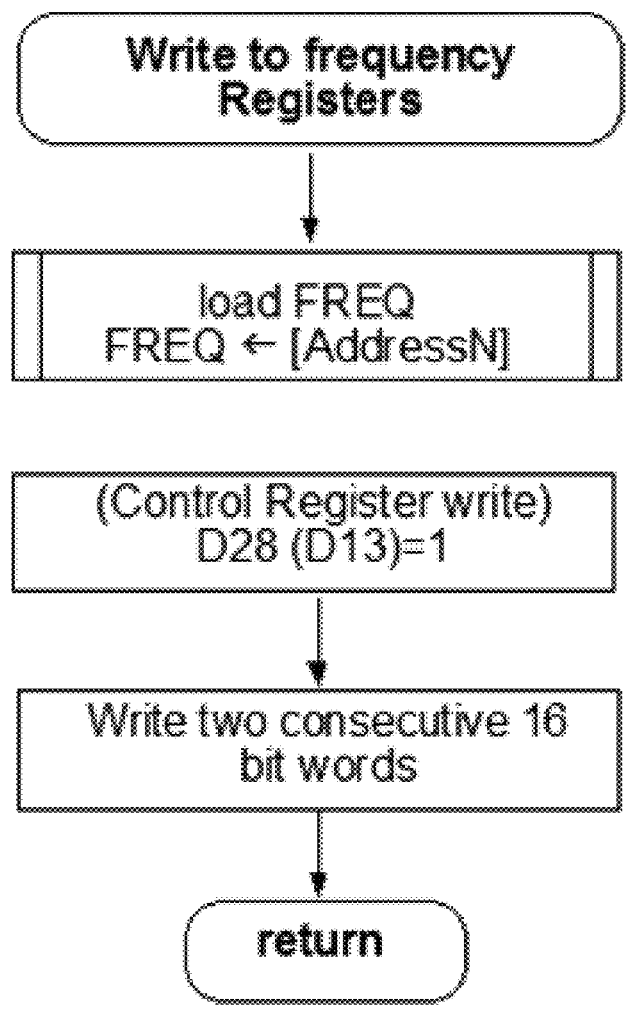
FIG. 19D is a flow diagram of the write to frequency registers subroutines.

The main program (FIG. 19A) of the microcontroller begins by setting all preliminary parameters (FIG. 19C) and initializing the DDS (FIG. 19B). The microcontroller then controls the frequency sweep of the signal being sent by the DDS, and stores the data of the reflected signal received from the RF-to-DC converter. The microcontroller then processes the information and displays it on a display (e.g., LCD).

The correspondence between the G_signal and the glucose level depends on many factors, including variation of location of placement in the external device, variations in the person's individual body characteristics, and external variations due to factors such as transpiration and temperature. All of these characteristics are taken into consideration during processing of the information, resulting in a calibration mode based on comparison. The calibration factor is also stored in the memory, allowing the use of this factor, or updating this, depending on the user. The following subroutine is executed at the beginning of the program or when an interrupt to modify calibration is set. The DDS is initialized by a reset and one frequency write procedure in order to function appropriately. During the writing to the DDS, FSYNC is low, as 16-bit data are written. The DDS undergoes an initialization, where the first frequency is written. The frequency is sent in two consecutive 16-bit words.

The flowcharts in FIGS. 19A-19D illustrate details of these procedures.

Hardware and Software Infrastructure Examples

The present invention may be embodied on various computing platforms that perform actions responsive to software-based instructions and most particularly on touch-screen portable devices. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++, Visual Basic or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It should be noted that when referenced, an "end-user" is an operator of the software as opposed to a developer or author who modifies the underlying source code of the software. For security purposes, authentication means identifying the particular user while authorization defines what procedures and functions that user is permitted to execute.

GLOSSARY OF CLAIM TERMS

Continuously monitoring a glucose level: This term is used herein to refer to a periodic or constant, long-term determination of the blood glucose level of a patient or subject.

Controller input: This term is used herein to refer to a device that is capable of entering or revising information or settings within the system.

Frequency sweep: This term is used herein to refer to scanning a radiofrequency band for detecting signals being transmitted within that band.

Near a blood vessel: This term is used herein to refer to the position of an implanted antenna in close enough proximity to a patient or subject's blood vessel that the resonant frequency experienced by the implanted antenna is affected by the glucose levels in the blood running through that blood vessel.

Passive sensing continuous glucose monitoring system: This term is used herein to refer to a non-invasive device that is capable of performing a periodic or constant, long-term determination of the blood glucose level of a patient or subject, where the determination is based on resonant frequency experienced by the implanted antenna.

Proximity: This term is used herein to refer to the state of two or more components being spatially near each other, or even adjacent to each other. For example, if a transmitting antenna and a receiving antenna are positioned in proximity to each other as discussed herein, they should be close enough to each other so as to not affect accurate transmission and receipt/reading of the radiofrequency signal through the implanted antenna.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A passive sensing continuous glucose monitoring system for continuously monitoring a glucose level in a patient or subject, comprising:
    an external transmitting antenna that is configured to be positioned outside of a body of said patient or subject, said transmitting antenna transmitting a radiofrequency signal into said body of said patient or subject;
    a passive internal antenna formed of silicon carbide and including an amorphous silicon carbide insulation, said internal antenna configured to be positioned subdermally in said patient or subject, said internal antenna receiving said radiofrequency signal from said transmitting antenna and configured to reflect said radiofrequency signal out of said body of said patient or subject, wherein a resonant frequency of said internal antenna varies as said blood glucose level in said patient or subject changes;
    an external receiving antenna that is configured to be positioned outside of said body of said patient or subject, said receiving antenna receiving said reflected radiofrequency signal from said internal antenna,
    wherein said external transmitting antenna and said external receiving antenna are disposed in proximity to each other, and said passive internal antenna is mounted directly towards said external transmitting antenna and said external receiving antenna;
one or more power sources for powering said external transmitting antenna and said external receiving antenna,
wherein said received radiofrequency signal is translated into a measure of said glucose level of said patient or subject;
a display for displaying said measure of said glucose level of said patient or subject.

2. A passive sensing continuous glucose monitoring system as in claim 1, wherein said transmitting antenna and said receiving antenna are disposed adjacent to each other.

3. A passive sensing continuous glucose monitoring system as in claim 1, wherein said transmitting antenna includes a microcontroller and a signal generator, wherein said microcontroller controls frequency and times of said signal generated by said signal generator, such that said microcontroller controls the frequency sweep transmitted by said transmitting antenna.

4. A passive sensing continuous glucose monitoring system as in claim 3, wherein said signal generator is a direct digital synthesis integrated circuit or a phase-locked loop with voltage control oscillator.

5. A passive sensing continuous glucose monitoring system as in claim 1, further comprising:
said receiving antenna including a microcontroller and a converter that converts radiofrequency power to direct current power (RF-to-DC converter),
said RF-to-DC converter receiving said reflected signal and converting said reflected signal to a digital value that is transmitted to said microcontroller,
said microcontroller storing said digital value in a storage module, processing said digital value into said glucose level, and displaying said glucose level on said display.

6. A passive sensing continuous glucose monitoring system as in claim 1, further comprising a controller input to control subsystem options, including calibration, storage, history, and default value restore.

7. A passive sensing continuous glucose monitoring system as in claim 6, wherein said controller input includes a keyboard.

8. A passive sensing continuous glucose monitoring system as in claim 1, wherein said transmitting antenna includes a signal generator, said receiving antenna includes a converter that converts radiofrequency power to direct current power (RF-to-DC converter), both of said transmitting antenna and said receiving antenna are in communication with a microcontroller, and said microcontroller is coupled to said display.

9. A passive sensing continuous glucose monitoring system as in claim 1, wherein said system operates in the industrial, scientific, and medical (ISM) radio band.

10. A passive sensing continuous glucose monitoring system as in claim 1, wherein said passive internal antenna is configured to be positioned in a fat layer of said patient or subject near a blood vessel of said patient or subject.

11. A method of continuously and passively sensing and monitoring a glucose level in a patient or subject, comprising the steps of:
making an incision in said patient or subject;
implanting a passive internal antenna subdermally into said patient or subject;
positioning an external transmitting antenna across from said implanted antenna outside of a body of said patient or subject;
positioning an external receiving antenna across from said implanted antenna outside of a body of said patient or subject, wherein said external receiving antenna is positioned in proximity to said external transmitting antenna;
mounting said passive internal antenna directly towards said external transmitting antenna and said external receiving antenna;
said external transmitting antenna generating and transmitting a radiofrequency signal into said body of said patient or subject;
said implanted antenna receiving said radiofrequency signal from said transmitting antenna and reflecting said radiofrequency signal out of said body of said patient or subject, wherein said passive internal antenna is formed of silicon carbide and includes amorphous silicon carbide insulation;
said external receiving antenna receiving said reflected radiofrequency signal from said implanted antenna and processing said received radiofrequency signal into a measure of said glucose level of said patient or subject;
displaying said glucose level of said patient or subject on a display,
wherein a resonant frequency of said internal antenna varies as said blood glucose level in said patient or subject changes.

12. A method as in claim 11, wherein said transmitting antenna includes a signal generator, said receiving antenna includes a converter that converts radiofrequency power to direct current power (RF-to-DC converter), both of said transmitting antenna and said receiving antenna are in communication with a microcontroller, and said microcontroller is coupled to said display.

13. A method as in claim 11, wherein said system operates in the industrial, scientific, and medical (ISM) radio band.

14. A method as in claim 11, wherein the step of implanting said passive internal antenna subdermally into said patient or subject is performed by positioning said passive internal antenna in a fat layer of said patient or subject near a blood vessel of said patient or subject.

15. A passive sensing continuous glucose monitoring system for continuously monitoring a glucose level in a patient or subject, comprising:
an external transmitting antenna that is positioned outside of a body of said patient or subject, said transmitting antenna transmitting a radiofrequency signal into said body of said patient or subject;
a passive internal antenna that is configured to be positioned subdermally in a fat layer of said patient or subject near a blood vessel of said patient or subject, said internal antenna receiving said radiofrequency signal from said transmitting antenna and reflecting said radiofrequency signal out of said body of said patient or subject, wherein a resonant frequency of said internal antenna varies as said blood glucose level in said patient or subject changes,
wherein said passive internal antenna is formed of silicon carbide and further includes amorphous silicon carbide insulation,
an external receiving antenna that is positioned outside of said body of said patient or subject, said receiving antenna receiving said reflected radiofrequency signal from said internal antenna,
wherein said external transmitting antenna and said external receiving antenna are disposed adjacent to each other, and said passive internal antenna is mounted directly towards said external transmitting antenna and said external receiving antenna, one or more power sources for powering said external transmitting antenna and said external receiving antenna, wherein said received radiofrequency signal is translated into a measure of said glucose level of said patient or subject, a display for displaying said measure of said glucose level of said patient or subject, said transmitting antenna including a signal generator being a direct digital synthesis integrated circuit, said receiving antenna including a converter that converts radiofrequency power to direct current power (RF-to-DC converter), both of said transmitting antenna and said receiving antenna being in communication with a microcontroller, said microcontroller controlling frequency and times of said signal generated by said signal generator, such that said microcontroller controls the frequency sweep transmitted by said transmitting antenna, said RF-to-DC converter receiving said reflected signal and converting said reflected signal to a digital value that is transmitted to said microcontroller, said microcontroller storing said digital value in a storage module, processing said digital value into said glucose level, and displaying said glucose level on said display to which said microcontroller is coupled;

a controller input to control subsystem options, including calibration, storage, history, and default value restore, wherein said controller input includes a keyboard, wherein said system operates in the industrial, scientific, and medical (ISM) radio band.

* * * * *